(12) United States Patent
Lundquist et al.

(10) Patent No.: US 10,517,655 B2
(45) Date of Patent: Dec. 31, 2019

(54) COMBINED INTRAMEDULLARY-EXTRAMEDULLARY BONE STABILIZATION AND ALIGNMENT SYSTEM

(71) Applicants: Andrew Lundquist, Edina, MN (US); Jonathan Fisher, Sandpoint, ID (US)

(72) Inventors: Andrew Lundquist, Edina, MN (US); Jonathan Fisher, Sandpoint, ID (US)

( * ) Notice: Subject to any disclaimer, the term of this patent is extended or adjusted under 35 U.S.C. 154(b) by 36 days.

(21) Appl. No.: 15/418,130

(22) Filed: Jan. 27, 2017

(65) Prior Publication Data

US 2017/0196602 A1 Jul. 13, 2017

Related U.S. Application Data

(63) Continuation-in-part of application No. 14/733,451, filed on Jun. 8, 2015.

(51) Int. Cl.
| | | |
|---|---|---|
| *A61B 17/72* | (2006.01) | |
| *A61B 17/17* | (2006.01) | |
| *A61B 17/80* | (2006.01) | |
| *A61B 17/88* | (2006.01) | |

(52) U.S. Cl.
CPC ...... *A61B 17/7291* (2013.01); *A61B 17/1728* (2013.01); *A61B 17/7233* (2013.01); *A61B 17/809* (2013.01); *A61B 17/8061* (2013.01); *A61B 17/8897* (2013.01)

(58) Field of Classification Search
CPC ...... A61B 17/72–7291; A61B 17/8891; A61B 17/1728
See application file for complete search history.

(56) References Cited

U.S. PATENT DOCUMENTS

| | | |
|---|---|---|
| 4,794,919 A | 1/1989 | Nilsson |
| 5,603,715 A | 2/1997 | Kessler |
| 6,248,109 B1 | 6/2001 | Stoffella |
| 6,355,041 B1 | 3/2002 | Martin |
| 9,005,255 B2 | 4/2015 | Lewis |
| 9,943,347 B2* | 4/2018 | Wayne .............. A61B 17/1725 |
| 2002/0143337 A1 | 10/2002 | Orbay |
| 2003/0040750 A1* | 2/2003 | Stoffella ............... A61B 17/68 606/324 |
| 2005/0033302 A1* | 2/2005 | Frank ..................... A61B 17/68 606/329 |
| 2005/0070902 A1 | 3/2005 | Medoff |
| 2009/0036931 A1* | 2/2009 | Pech .................. A61B 17/1725 606/280 |
| 2010/0274245 A1 | 10/2010 | Gonzalez-Hernandez |
| 2012/0245642 A1 | 9/2012 | Giannoudis |
| 2014/0066995 A1* | 3/2014 | McCormick ....... A61B 17/1728 606/281 |

(Continued)

*Primary Examiner* — Jacqueline T Johanas
(74) *Attorney, Agent, or Firm* — Wells St. John P.S.

(57) ABSTRACT

Disclosed is a combined intramedullary and extramedullary bone stabilization and alignment system, which includes both methods and apparatuses for the alignment and stabilization of a first bone or piece of bone to a second bone or piece of bone. Embodiments of the system may include an implant device which has an elongated framework within the intramedullary portion and an extramedullary portion which are cannulated. The cannulated aspect of the framework includes a wire aperture through both the intramedullary portion and the extramedullary portion.

12 Claims, 21 Drawing Sheets

(56) References Cited

U.S. PATENT DOCUMENTS

| | | | |
|---|---|---|---|
| 2015/0073414 A1 | 3/2015 | Rogachefsky | |
| 2016/0022340 A1* | 1/2016 | Wayne | A61B 17/1725 606/304 |
| 2016/0354127 A1* | 12/2016 | Lundquist | A61B 17/7233 |
| 2017/0196602 A1 | 7/2017 | Lundquist | |
| 2018/0028242 A1* | 2/2018 | Parekh | A61B 17/8061 |
| 2018/0070995 A1* | 3/2018 | Kay | A61B 17/7291 |

* cited by examiner

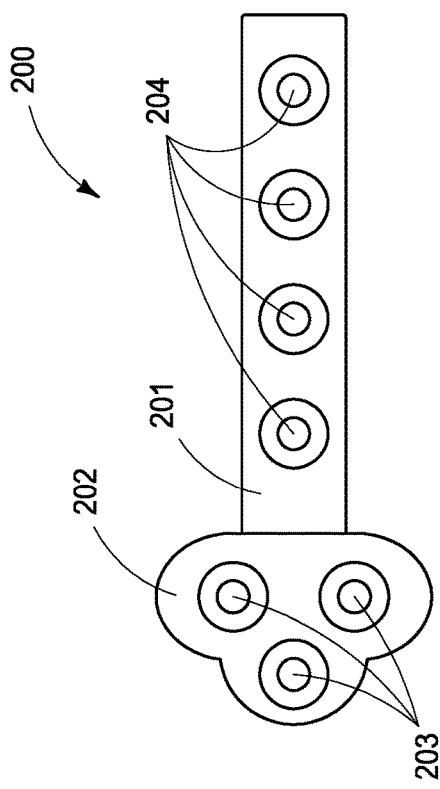
FIG. 10A
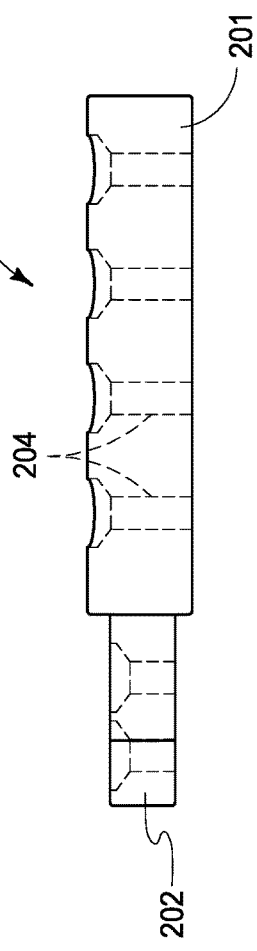
FIG. 10B
FIG. 10
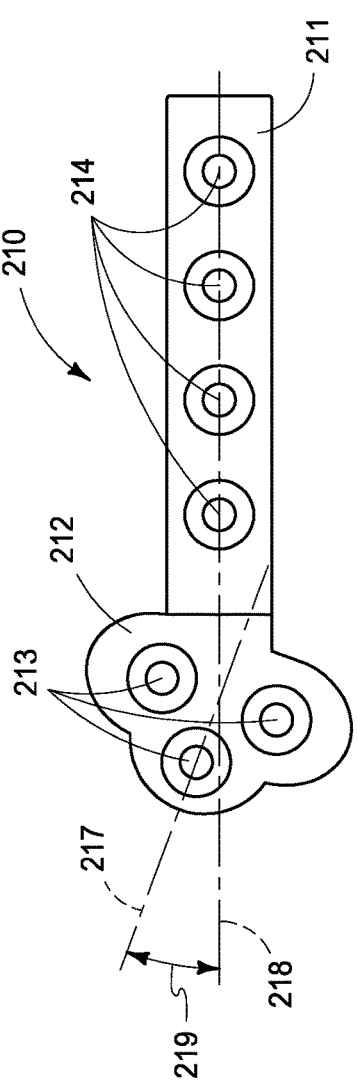
FIG. 11

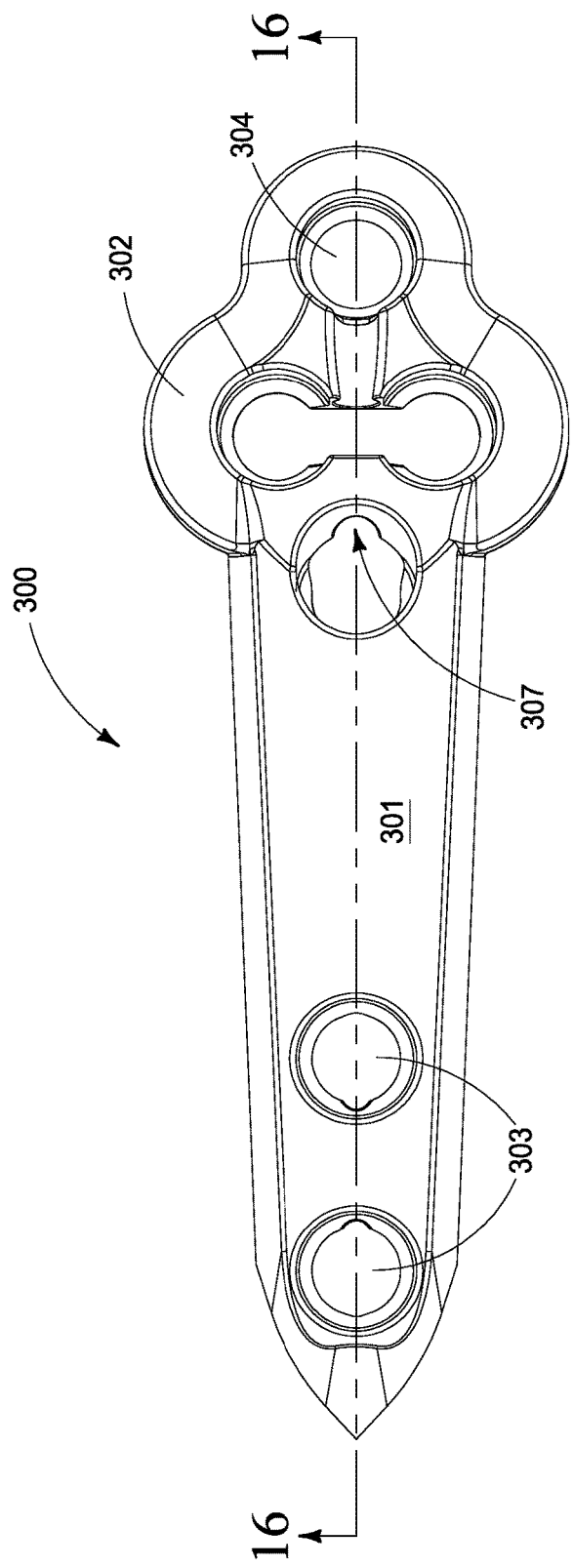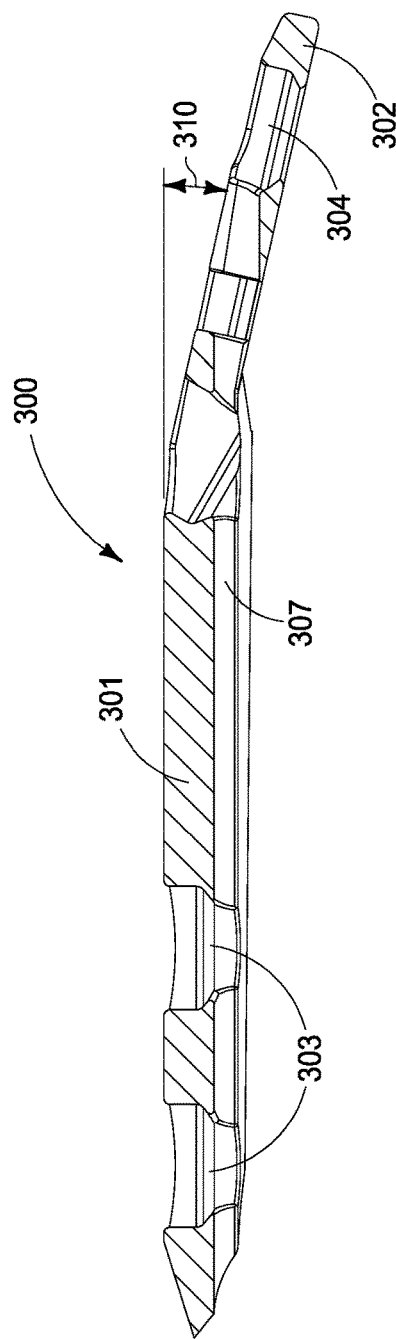
FIG. 15
FIG. 16

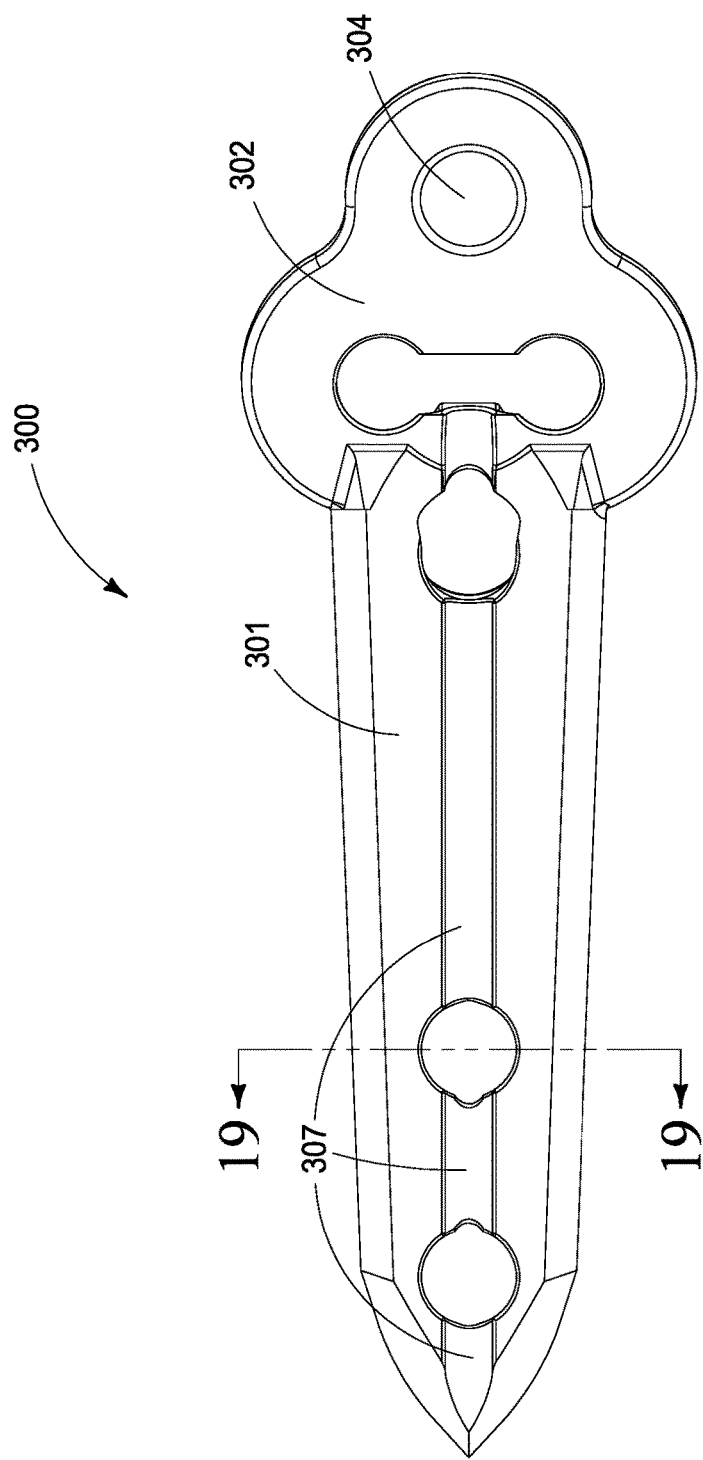
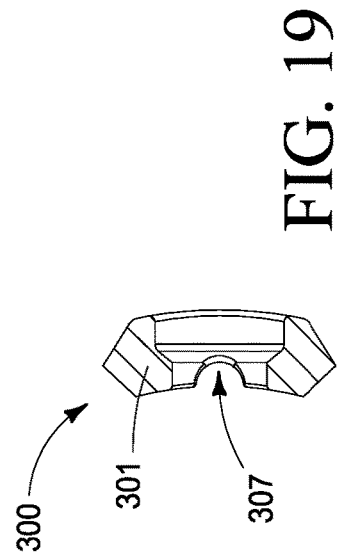
FIG. 18
FIG. 19

COMBINED INTRAMEDULLARY-EXTRAMEDULLARY BONE STABILIZATION AND ALIGNMENT SYSTEM

CROSS REFERENCE TO RELATED APPLICATION

This application claims the benefit of U.S. patent application Ser. No. 14/733,451, filed Jun. 8, 2015.

TECHNICAL FIELD

This invention pertains to a combined intramedullary and extramedullary stabilization and alignment system for use on the bones and joints of mammals.

BACKGROUND OF THE INVENTION

For many years numerous surgical procedures have been performed to stabilize and align (or re-align) parts of the skeletal structure of mammals. These surgeries include the alignment of existing joints as well as the fusion or attachment of one part of a bone to another part of a bone that have been separated surgically or otherwise. A surgical osteotomy for example is a procedure where a bone is cut to change the alignment (lengthen, shorten or otherwise change).

Bunion and/or hallux valgus surgeries are examples of applications for some embodiments of this invention wherein a bone is surgically cut or separated into two pieces or portions (osteotomy), and then surgically fixed back together in a more desired multi-planar and/or rotational alignment and stabilization. "Hallux" is used as another name for a person's big toe, and generally includes two bones or "phalanges" and valgus generally refers to a deformation of a bone or joint. The term "hallux valgus" typically refers to a deviation of the big or great toe toward the inside portion or fibular border of the foot.

An example of this type of surgical procedure relates to bunion surgery, which may also be referred to as a bunionectomy or a surgical procedure to correct or relieve a bunion. A bunion is a distortion or enlargement of a joint in the big toe which causes the big toe to curve outwardly toward the other toes in the foot. The metatarsal bone protrudes medially and can rotate externally (see FIG. 1).

In a typical foot the first intermetatarsal angle is in the five to ten degree range (generally under fifteen degrees), whereas in a foot with metatarsus primus varus, the first intermetatarsal angle may be greater than fifteen degrees and can increase to twenty degrees or more. The "first" intermetatarsal angle is the angle between the first and second metatarsal bones. A metatarsus primus varus is a condition in which the first metatarsal bone has an increased angle away from the second metatarsal bone and some rotational distortion.

Some estimate there are approximately two-hundred thousand to four-hundred thousand bunion or Hallux Valgus (HV) surgical procedures performed every year. Metatarsus primus generally occurs along with bunion and hallux valgus.

The difficulties with some of the prior art surgical procedures are multiple and many modifications of the basic procedure have been proposed and explored. However, despite the years of attempts to modify the bunionectomy, there is still a relatively high rate of patient dissatisfaction with bunion and hallux valgus types of surgeries.

In the bunion surgery example the deformity most often addressed by the surgical procedure is the increase in the angle between the first and second metatarsals, an example of which is illustrated in FIG. 1 (angle 93). The view of the deformity shown in FIG. 1 only shows one plane of deformation whereas in most bunion conditions the patient has deformity in multiple planes and some further include rotational deformity (angle 94, FIG. 1). In the prior art these deformity angles may be referred to as the first intermetatarsal angle ("IMA") and the second intermetatarsal angle, with the first intermetatarsal angle being the angle between the first and the second metatarsal bones.

It is believed that in many bunion surgeries the failure to recognize and/or solve the frontal plan rotation deformation for example, results in less than desirable surgical results. The prospects for a successful surgical procedure are further limited by the difficulties associated with the imprecise nature of being able to more precisely view and align the two part/portions of the bones or portions/parts/pieces of bones being fixed together (or the joint being re-aligned).

Only a few of the existing surgical procedures or systems address both the translational and rotational deformity issues. One of the most common surgical procedures used to address the translational and rotational deformity issues is referred to as a Lapidus Bunionectomy, in which the first metatarsal is fixed to the medial cuneiform. Unfortunately the Lapidus Bunionectomy has historically had a four to six week non-weight bearing postoperative healing period.

Despite the longstanding and recognized need for an improved system to address the various deformities and/or issues typically associated with skeletal or bone misalignment and/or deformity in mammals, there is still a need for an improved system.

Aspects of this invention such as the cannulated aspect of the implant device have an advantage of providing the surgeon an additional alignment tool for use during the surgery in combination with what is referred to as a wire or "K-wire". The term K-wire is used broadly in the surgical field to refer to a wire or pin that may have numerous deviations (sharpened portions, threaded portions, various or varying thicknesses, etc). K-wires were originally referred to as Kirschner wires because Martin Kirschner was originally credited with the introduction of the wires into surgery in the early 1900's.

In surgeries, K-wires may be conveniently used for temporary or permanent fixation. In some applications K-wires may first be inserted into one part or portion of the bone or joint, and then the intramedullary and extramedullary portions of one embodiment of the invention can be slid over the K-wire to achieve more consistent improved alignment of the device. This will lead to more consistent desired (or improved) alignment of the joint and/or fusion.

There are substantial opportunities in these types of surgeries for improvement in the precise placement and fixation of the metatarsal head, to meet two objectives of the surgery, namely the centering of the metatarsal head over the sesamoid, and the angular alignment or rotational adjustment to reduce the angle between the first and second metatarsals.

Generally, after the implant device is attached to the metatarsal head it is oftentimes desirable, but not very feasible under current technology, to make micro-adjustments to manipulate or move the metatarsal head laterally or rotationally/angularly. Embodiments and aspects of this invention provide the surgeon with the ability to make these lateral and rotational micro-adjustments to, for example, center the metatarsal head over the sesamoid or the sesamoid apparatus and to make the desired rotational or angular adjustment. At this stage of the surgery an axial view of the sesamoid may provide the surgeon the image to allow the surgeon to accurately see how much rotation or angular adjustment may be needed in order to micro adjust the metatarsal head into as near to the exact position as can be accomplished. The current technology heretofore has not provided a sufficient ability (or any ability) to make such micro-adjustments, including using the sesamoid at axial view.

Aspects of this embodiment provide a new and novel ability to make post-attachment adjustments to position the metatarsal head, by providing a system which allows the surgeon to make post plate attachment adjustments to position the metatarsal head laterally and rotationally/angularly.

It is therefore an object of aspects or embodiments of this invention to provide a system and tool whereby post attachment adjustments (including micro adjustments) can be made to finally position or fixate the metatarsal head laterally and rotationally/angularly more accurately.

It is a further object of some embodiments of this invention to provide an adjustment tool, integral with or separate from the drill and/or wire guide or template, is attachable and detachable to and from the implant device, to provide for the post metatarsal head attachment adjustment of the position (such as lateral position) and the angular position of the metatarsal head.

It is therefore an object of some embodiments of this invention to provide an improved stabilization and/or alignment system which may be used to address bone and joint alignment issues generally, and which may include foot related bunion and unwanted metatarsal deformations.

It is a further object of this invention to provide such system which provides an improved alignment tool during the surgical procedure, such as by providing a cannulated intramedullary portion that is disposed to be inserted into a bone over the wire or k-wire as a guide. It is a further object to provide such a system wherein the extramedullary portion is also cannulated.

Other objects, features, and advantages of this invention will appear from the specification, claims, and accompanying drawings which form a part hereof. In carrying out the objects of this invention, it is to be understood that its essential features are susceptible to change in design and structural arrangement, with only one practical and preferred embodiment being illustrated in the accompanying drawings, as required.

BRIEF DESCRIPTION OF THE DRAWINGS

Preferred embodiments of the invention are described below with reference to the following accompanying drawings.

FIG. 5 is a top skeletal schematic representation of bones in a typical human foot, illustrating an example of an implant device contemplated by embodiments of this invention, wherein a drill guide or template is used to align the drilling of a transverse fastener aperture through the fastener aperture in the intramedullary portion of the implant, for the later insertion of a screw there-through;

FIG. 10 constitutes FIGS. 10A and 10B, which are different views of another embodiment of an implant device contemplated by embodiments of this invention;

FIG. 10A is top view and FIG. 10B is an elevation view of an example of another embodiment of an implant device contemplated by this invention;

FIG. 11 is a top view of an example of an embodiment of this invention wherein the intramedullary portion of the implant device is at an angle relative to the extramedullary portion;

FIG. 13 is top skeletal schematic representation of bones in a typical human foot, illustrating an example of an angled implant device (such as shown in FIG. 12) contemplated by embodiments of this invention, wherein a drill guide or template is used to align the drilling of a transverse fastener aperture through the fastener aperture in the intramedullary portion of the implant, for the later insertion of a screw there-through;

FIG. 15 is a top view of the example of the implant device illustrated in FIG. 14;

FIG. 16 is a front view of the example of the implant device illustrated in FIG. 14;

FIG. 18 is a bottom view of the example of the implant device illustrated in FIG. 14;

FIG. 19 is section view 19-19 from FIG. 18;

DETAILED DESCRIPTION OF THE PREFERRED EMBODIMENTS

Many of the fastening, connection, manufacturing and other means and components utilized in this invention are widely known and used in the field of the invention described, and their exact nature or type is not necessary for an understanding and use of the invention by a person skilled in the art or science; therefore, they will not be discussed in significant detail. Furthermore, the various components shown or described herein for any specific application of this invention can be varied or altered as anticipated by this invention and the practice of a specific application or embodiment of any element may already be widely known or used in the art or by persons skilled in the art or science; therefore, each will not be discussed in significant detail.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

Although the embodiments of this invention as applied to certain foot surgeries is primarily discussed to describe the invention, it will be noted by those of ordinary skill in the industry that the methods and apparatuses disclosed in this invention may be utilized in other bone related applications. For example, while the application discussed is a metatarsal osteotomy, it may be applied to osteotomies on other bones or pieces/parts of bones as well. Aspects of this invention may also be used to stabilize or fix two different bones together, including two bones comprising a joint. Still further embodiments of this invention may be utilized in fixing, stabilizing and/or aligning two portions/parts/pieces of bones, all within the contemplation of embodiments of this invention.

Figure 1:
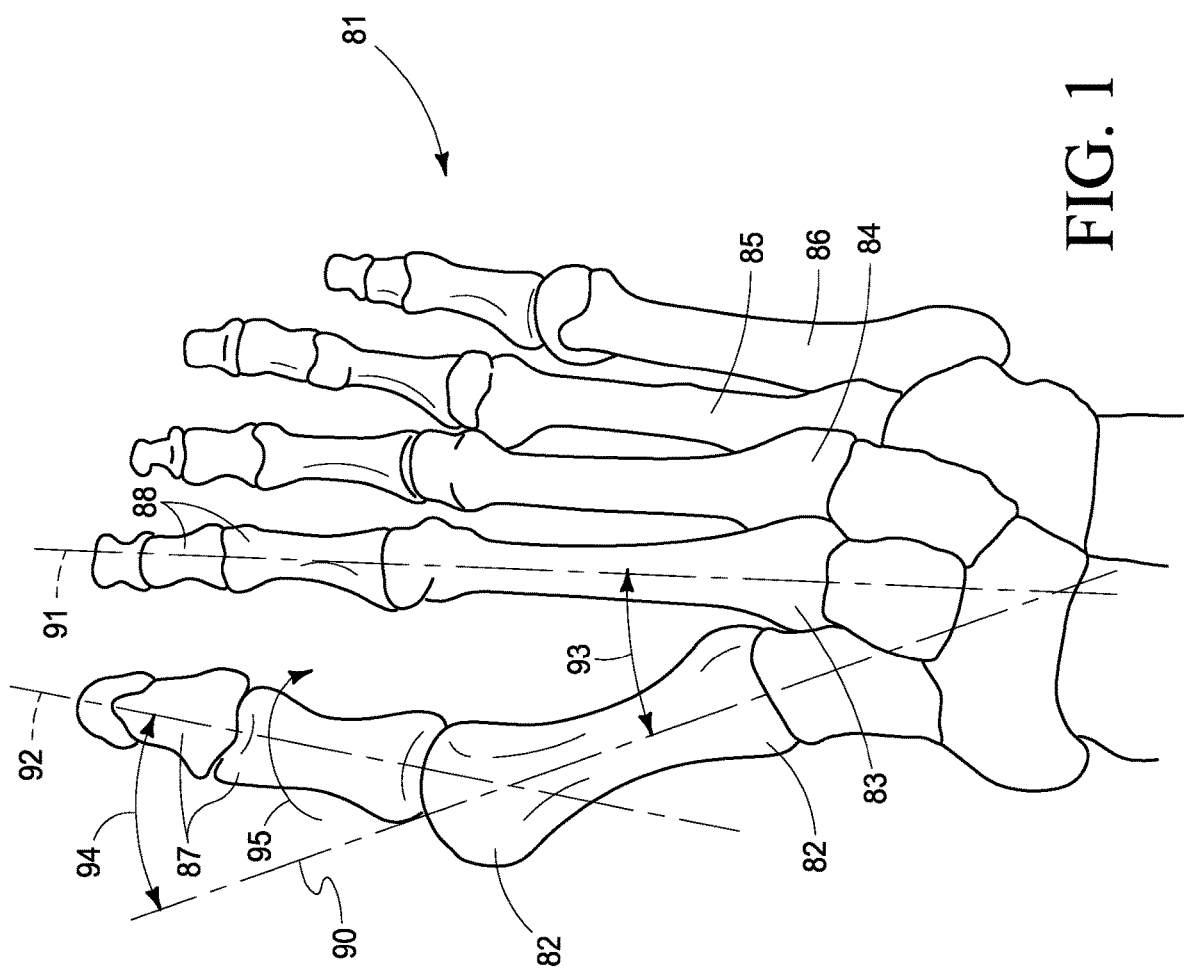
FIG. 1 is a top view of bones in a typical human foot illustrating bunion and metatarsal issues.

FIG. 1 is a top view of bones in a typical human foot 81 illustrating bunion and metatarsal issues. FIG. 1 shows first metatarsal bone 82, second metatarsal bone 83, third metatarsal bone 84, fourth metatarsal bone 85 and fifth metatarsal bone 86 of foot 81. FIG. 1 also shows the pair of first phalange bones 87 and second pair of phalange bones 88 for the second or middle toe.

FIG. 1 illustrates the approximate center line 90 of the first metatarsal bone 82 as item 90, the approximate center line 92 for the phalange bones 87 for the first toe and the approximate center line 91 for the second metatarsal bone 83. Angle 93 would represent the first intermetatarsal angle ("IMA") and angle 94 would represent an amount that the phalanges rotated relative to the first metatarsal bone 82, while arrow 95 may be indicative of further rotation of that portion of the big toe.

Figure 2:
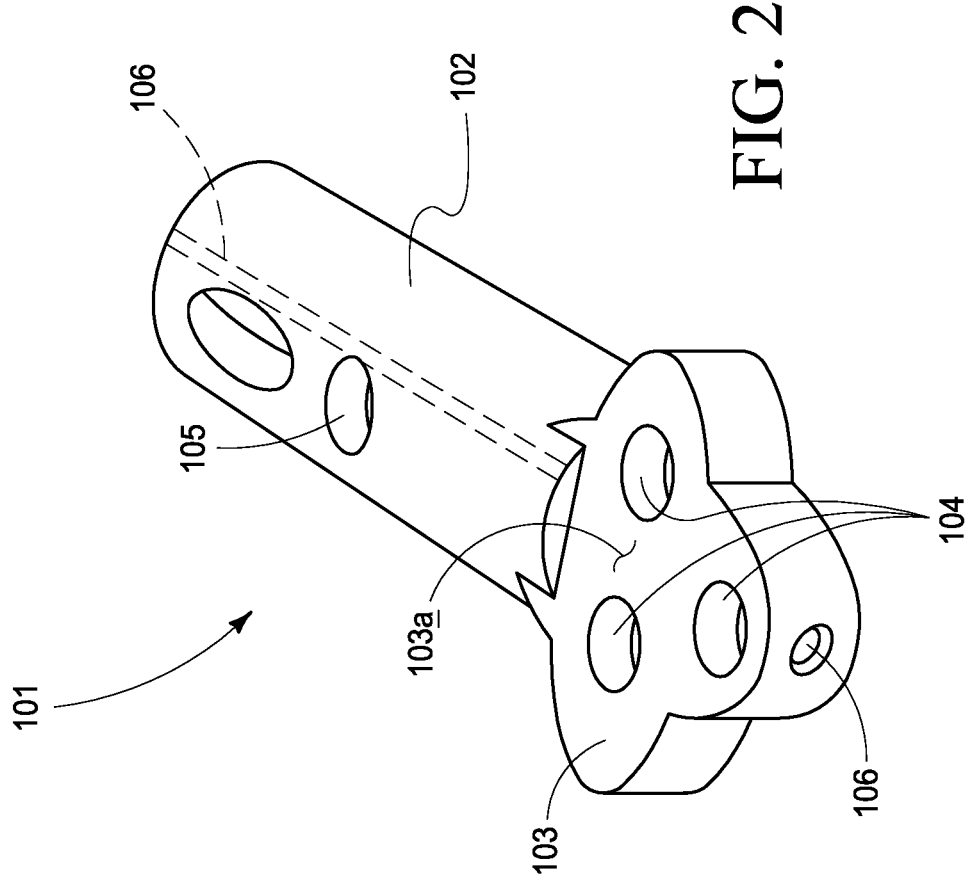
FIG. 2 is a perspective view of an example of one embodiment of an implant device contemplated by this invention.

FIG. 2 is a perspective view of an example of one embodiment of an implant device 101 contemplated by this invention, illustrating the framework with the intramedullary portion 102, extramedullary portion 103, and the K-wire aperture 106 through both the intramedullary portion 102 and the extramedullary portion 103.

FIG. 2 further illustrates fastener apertures 104, and an abutment surface 103*a* which, in some embodiments of this invention, may be configured for abutment with a portion of the second piece of the metatarsal bone to which it is intended to be fastened. The intramedullary portion 102 also includes transverse aperture 105.

In some embodiments of this invention, the intramedullary portion of the apparatus may be partially or fully inserted into the center or medulla portion of the bone, first bone or first section or piece of the bone.

In this application the term plate as used is not limited to any particular geometric shape such as a flat bodied portion, but instead is broader than that and may include different and other shapes and configurations.

Figure 3:
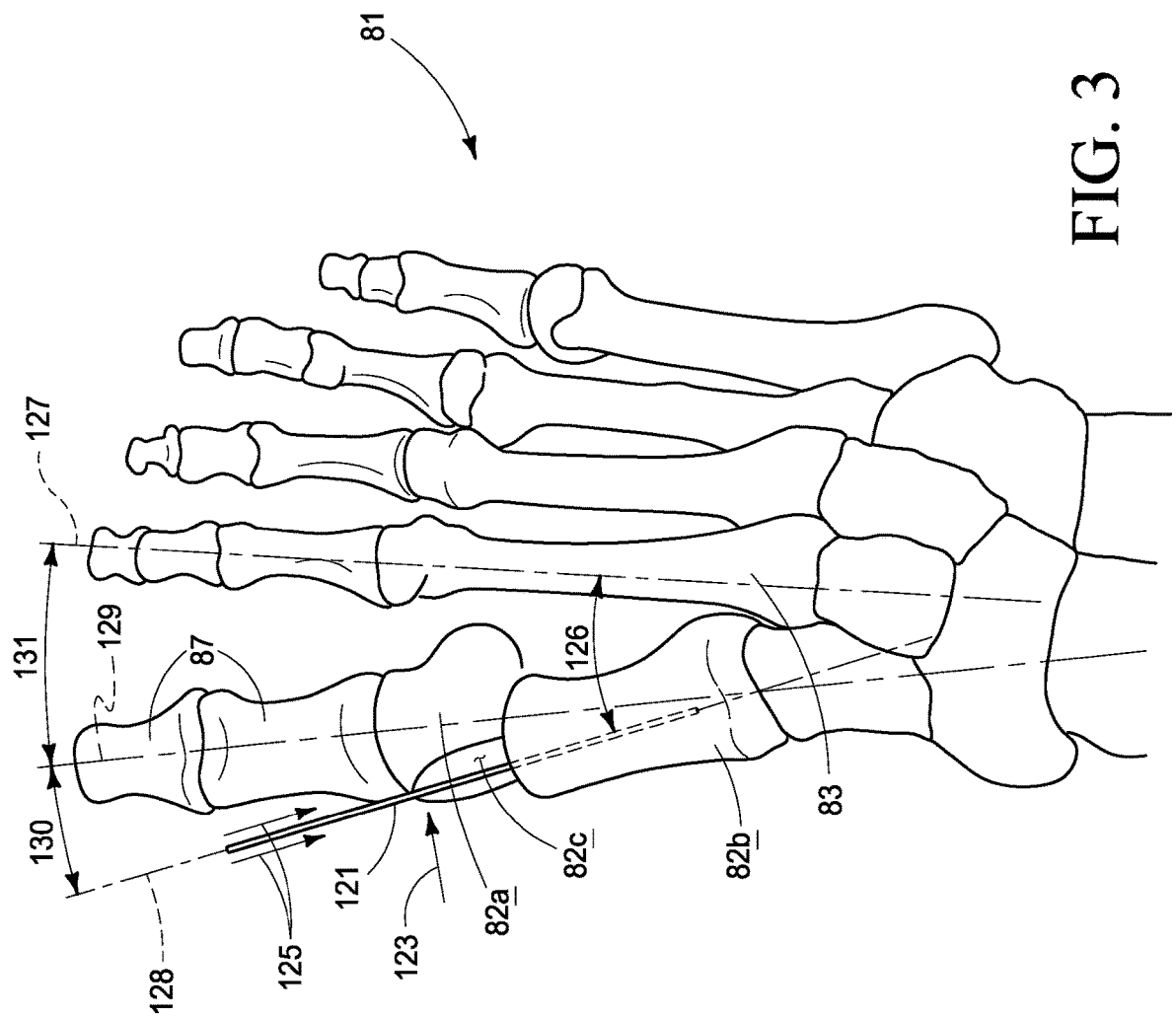
FIG. 3 is a top skeletal schematic view of bones in a typical human foot illustrating a first metatarsal bone that has been cut or severed transversely and a K-wire inserted into a first piece of the first metatarsal bone.

FIG. 3 is a top skeletal schematic view of bones in a typical human foot 81 illustrating a first metatarsal bone 82 (shown in FIG. 1) having been transversely cut and a K-wire 121 inserted into a first piece 82*b* of the first metatarsal bone. FIG. 3 also illustrates first intermetatarsal angle 126 between the approximate center line of the first metatarsal bone and the approximate centerline 127 of the second metatarsal bone 83.

FIG. 3 shows a second piece 82*a* of the first metatarsal bone 82 (shown in FIG. 1) which has been cut, sawed or severed from first piece 82*b* of the first metatarsal bone as part of the surgical procedure. The second piece 82*a* of the metatarsal bone also includes surface 82*c*, which may have been prepared or reformed by cutting, sawing and/or grinding to provide an interface surface for the implant device (shown in other figures) to abut, fasten to and otherwise interact with.

Once the first metatarsal bone 82 (shown in FIG. 1) has been cut or sawed into a first bone piece 82*b* and a second bone piece 82*a* of the first metatarsal bone, and the desired surface area 82*c* has been cut into the second piece 82*a* of the first metatarsal bone, the second piece 82*a* of the first metatarsal bone 82 may be moved toward the second metatarsal bone 83 as illustrated by arrow 123.

The second piece 82*a* of the first metatarsal bone 82 shown in FIG. 3 would be relocated (represented by arrow 123) to a location which would produce the desired or preferred alignment of the big toe or Halux. Once the second piece 82*a* of the first metatarsal bone 82 is placed at the desired angular and alignment location, the K-wire 121 may be implanted, inserted or forced (arrows 125) into the first piece 82*b* of the first metatarsal bone 82 at a desired angle to enable the implant device (item 99, FIG. 4) to be inserted over the K-wire 121 and provide the desired angle for the big toe or Hallux.

FIG. 3 further illustrates a new center line 129 for the big toe, which is angle 130 from the prior center line 128 of the first metatarsal bone 82, and now only angle 131 offset from the centerline 127 of the second metatarsal bone 83.

In the embodiments which make use of a K-wire, this may eliminate the need to drill a hole through the bone but instead the K-wire can be more efficiently inserted through other known means with less or minimal negative effects to the bone of the patient. It will be appreciated by those of ordinary skill in the art that while a K-wire is referred to herein, this invention is not so limited as it includes a pin, wire, thin rod or other similar alignment component.

It will further be appreciated that the insertion of the K-wire into, for example, the first metatarsal piece may be accomplished in any one of a number of different ways known in the art, such as forced insertion, screwing or through the use of tools, all within the contemplation of this invention and with no one in particular being required to practice this invention.

In the prior art situations in which a K-wire is used for temporary alignment of the two pieces of bone, the wire must be removed before a fixation device may be removed. The removal of the K-wire makes it much more difficult to consistently get as precise of an alignment as desired for the resulting fixed bone sections. In embodiments of this invention and because of the wire aperture or cannulated feature of this invention, the K-wire or wire aperture can be slid over the K-wire to position, align and guide the implant device to its desired and aligned location. During the alignment process the surgical area (and the alignment and position) of the K-wire can be readily seen through use of x-ray device to further assist in more precisely obtaining the desired angles.

Figure 4:
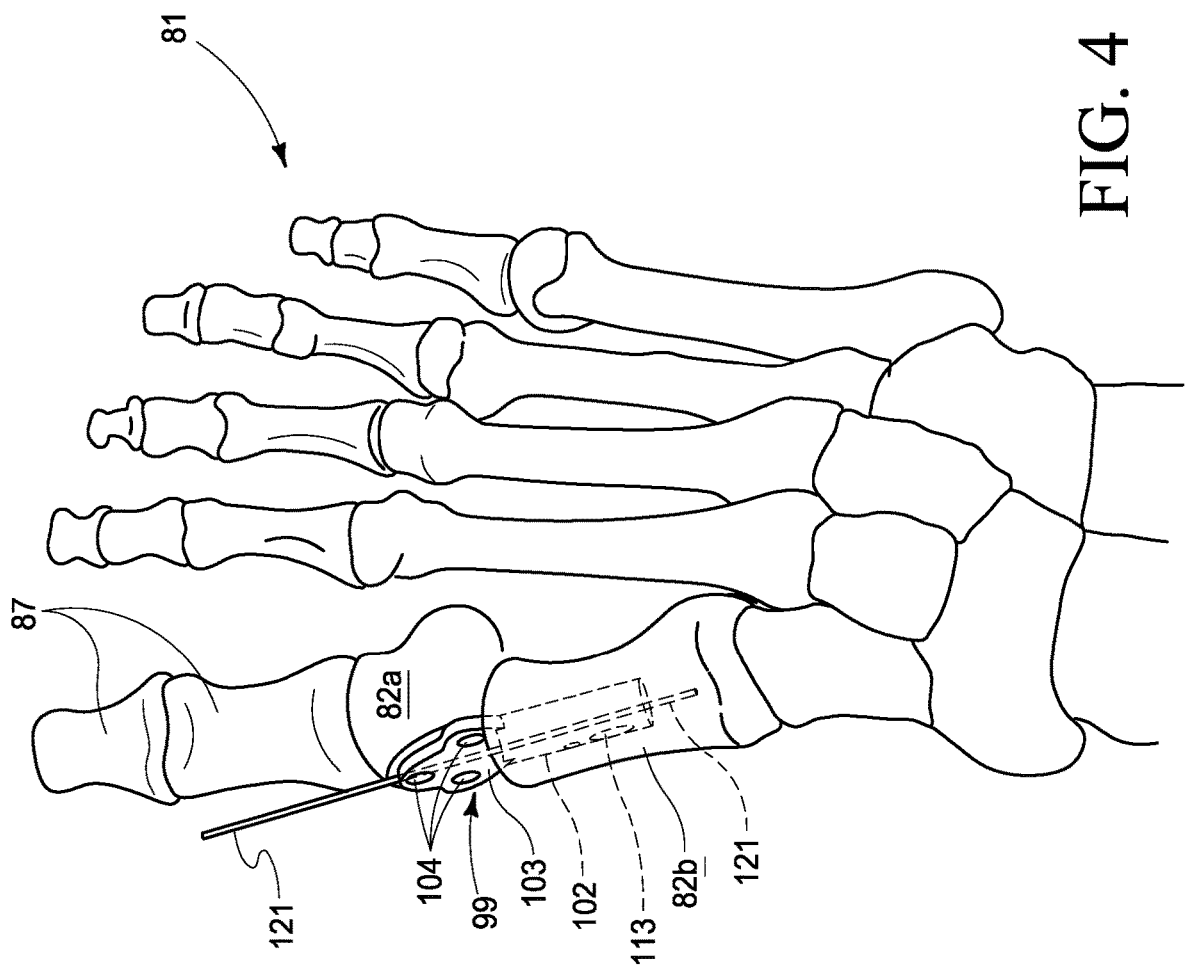
FIG. 4 is a top skeletal schematic representation of bones in a typical human foot, illustrating an example of an implant device contemplated by embodiments of this invention, with the intramedullary portion inserted over the K-wire and into the first piece of the first metatarsal bone piece and abutting or alongside the second metatarsal bone piece.

FIG. 4 is a top skeletal schematic representation of bones in a typical human foot 81, illustrating an example of an implant device 99 contemplated by some embodiments of this invention, with the intramedullary portion 102 inserted over the K-wire 121 and into the first piece 82b of the first metatarsal bone, and the extramedullary portion 103 of the implant device 99 abutting or alongside the prepared surface (shown as item 82c in FIG. 3) in the second piece 82a of the first metatarsal bone 82. FIG. 4 further shows a transverse screw aperture 99 for the transverse insertion of a screw through the bone and the intramedullary portion 102.

FIG. 4 shows how the K-wire 121 serves as an initial alignment aid and then as the guide inserting or implanting the intramedullary portion 102 at the desired angle. It will be appreciated by those of ordinary skill in the art, the benefits and advantages of utilizing the K-wire 121 for the alignment or re-alignment. Current practice requires the surgeon under more difficult circumstances to more roughly estimate the alignment when inserting plates and other devices that are currently used as part of these types of surgeries.

Figure 5:
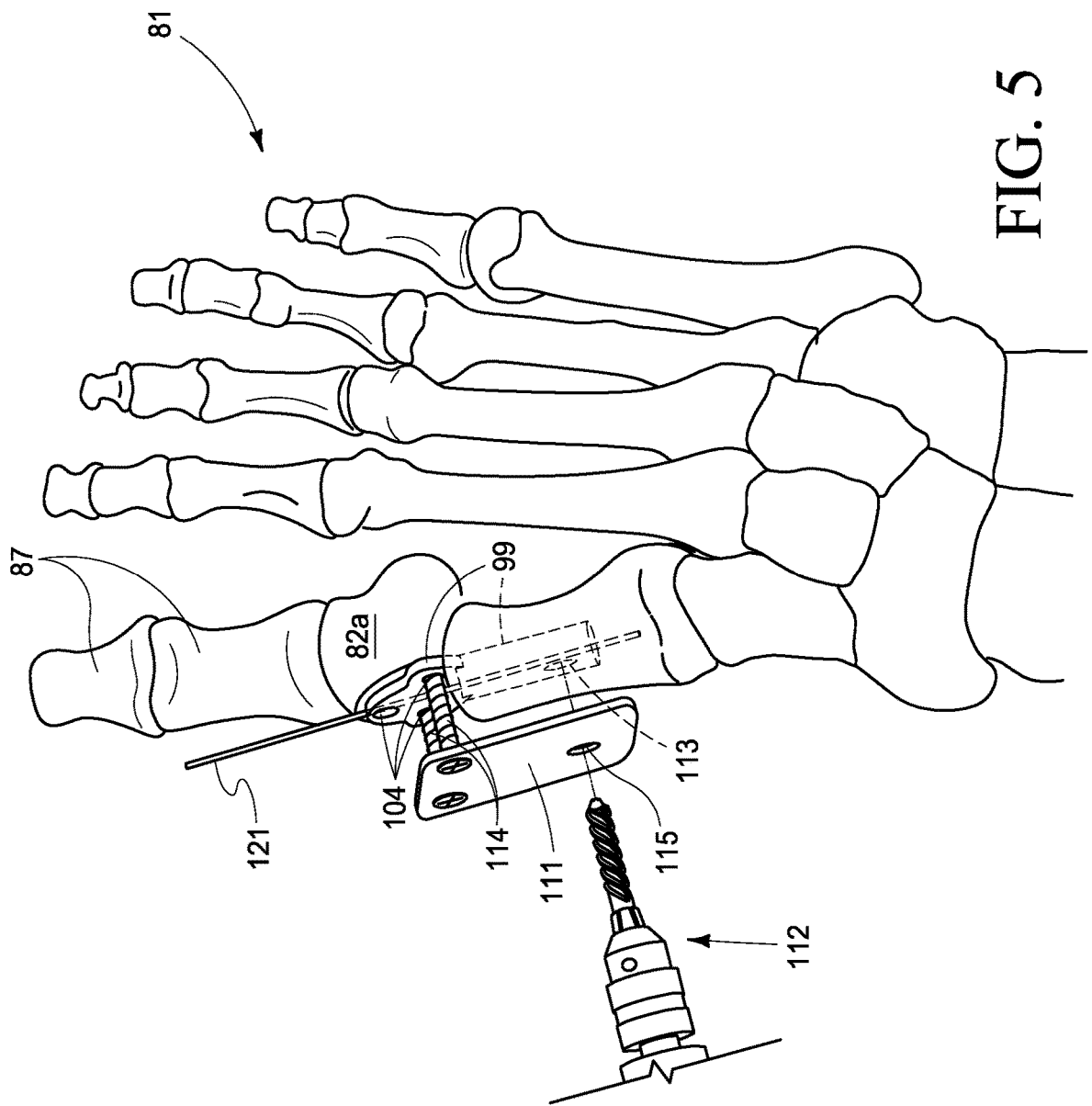
Figure 6:
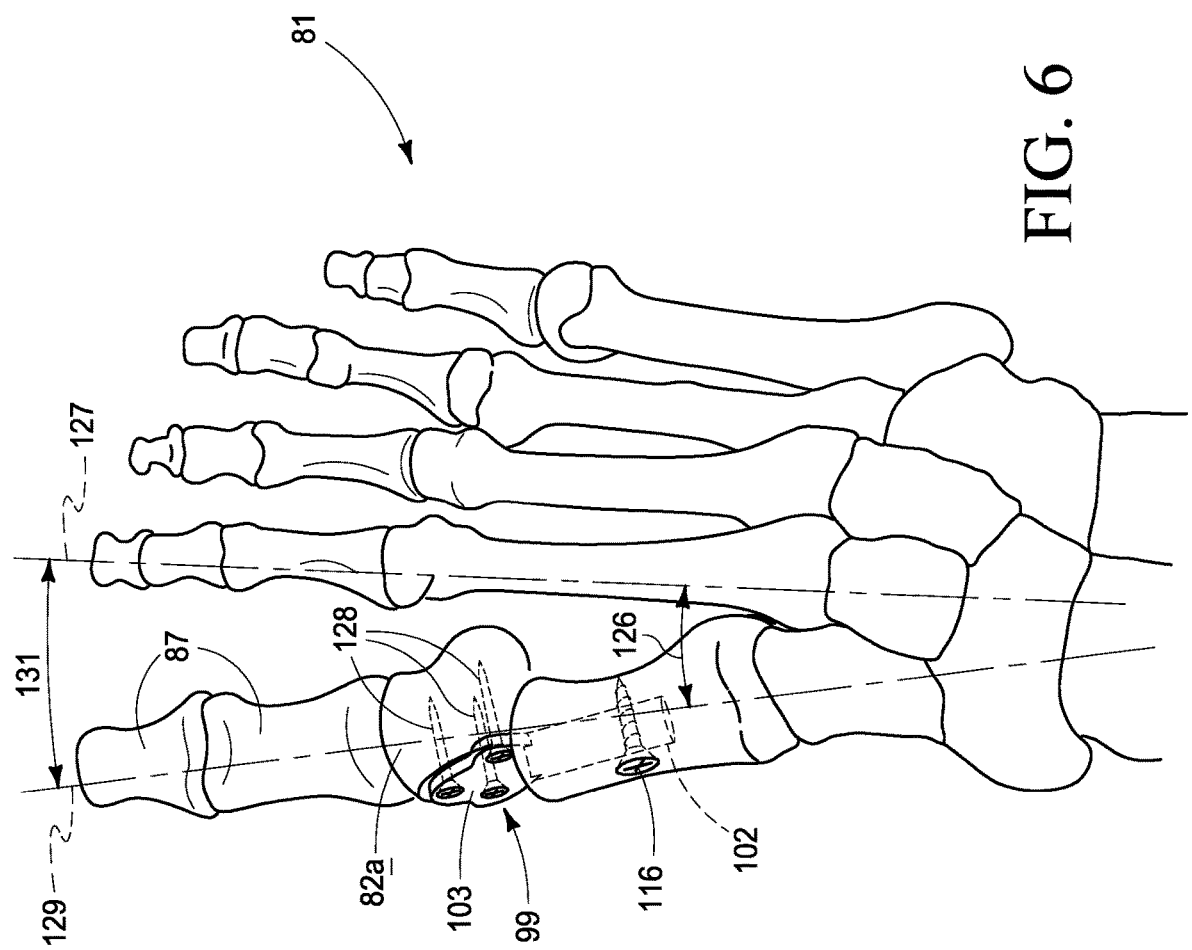
FIG. 6 is a top skeletal schematic representation of bones as shown in FIG. 4, and further illustrating bone fasteners secured within the second piece of the first metatarsal bone.

FIG. 5 is a top skeletal schematic representation of bones in a typical human foot, illustrating an example of an implant device 99 contemplated by embodiments of this invention, wherein a drill guide or template 111 is used to align the transverse drilling of a pilot hole through the bone and through a transverse screw aperture 113 in the intramedullary portion of the implant device 99, for the later insertion of a screw (as shown in FIG. 6). The drill guide 111 is a template to provide sufficient guidance and alignment of the drill 112 through drill hole 115 in the drill guide such that the hole drilled through the bone aligns with the transverse screw or fastener aperture 113 in the intramedullary portion of the implant device. While the alignment example shown in FIG. 5 illustrates the use of two screws 114 which fix the drill guide 111 relative to the implant device 99, other alignment mechanisms or tools may be utilized within the contemplation of embodiments of this invention, with no one being required to practice this invention.

FIG. 6 is a top skeletal schematic representation of the foot 81 as shown in FIG. 4, and further illustrates bone fasteners 128 (screws in the example of the embodiment shown) that have been placed through the fastener apertures 104 (shown in FIG. 4) in the extra-medullary portion 103 of the implant device 99 and secured or fastened within the second piece 82a of the first metatarsal bone. Bone fastener 116, a screw in this example, is shown transversely screwed into the bone through the screw aperture in the intramedullary portion 102 of the implant device 99. FIG. 6 also shows phalange bones 87 of the big toe, as well as the new angle 131 between the new centerline 129 of the big toe and the centerline 127 of the second toe.

It will be noted and appreciated by those of ordinary skill in the art that this invention is not limited to any one particular bone fastener, but instead any one of a number of known and to be discovered bone fasteners may be utilized within the contemplation of this invention, such as without limitation, bone screws, bone nails and the like.

Figure 7:
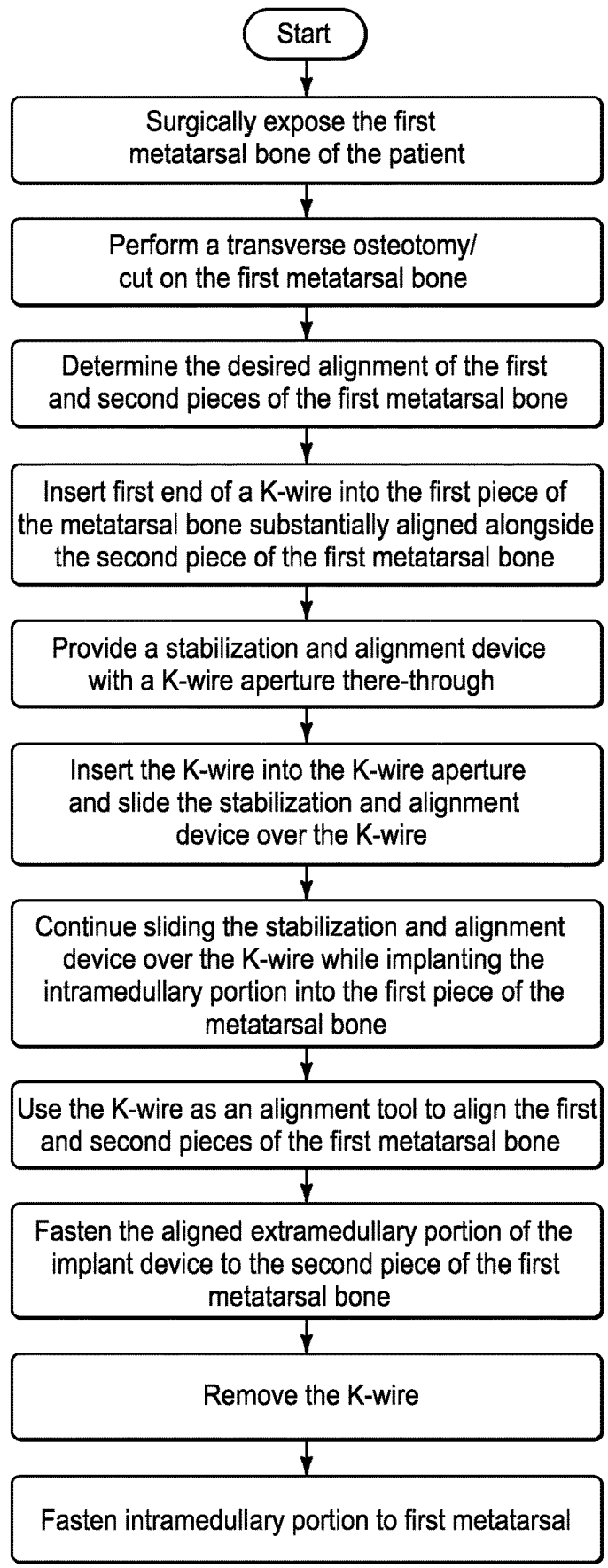
FIG. 7 is a box diagram flow chart of an example of a method or process contemplated by embodiments of this invention.

FIG. 7 is a box diagram flow chart of an example of a method or process contemplated by embodiments of this invention. The first step in FIG. 7 is the beginning of a surgery in which the patient's tissue must be parted in order to expose the first metatarsal bone of the patient's foot to provide sufficient vision and clearance for the remaining steps of the surgical alignment and stabilization process, as well as the installation of the implant device.

The next step involves the transverse cutting, sawing or severing of the first metatarsal bone of the patient into at least a first piece and a second piece. Then the second piece of the first metatarsal bone is placed into the desired alignment with the first piece of the first metatarsal bone for the desired angular result, as shown in FIG. 3.

There is an intermediate elective next step that may be and is preferably performed, and that is preparing a surface on the second piece of the first metatarsal bone to better receive and interact with the extramedullary portion of the implant device. It is preferred to create a flat surface on the second piece of the first metatarsal bone to provide a surface or interface to which the extramedullary portion of the implant device can be fastened. The surface may be prepared by grinding or cutting tools or in other ways customary in the trade.

The first end of a wire may then be inserted or implanted within the first piece of the first metatarsal bone, aligning the second end of the wire substantially alongside the second piece of the first metatarsal bone surface to which the extramedullary portion of the implant device will be fastened or attached. It is without limitation at this approximate stage that the benefits of utilizing a wire for alignment combined with a cannulated implant device can be achieved. The wire may be utilized through x-rays or visual observation to obtain the desired alignment of not only the first and second pieces of the first metatarsal bone, but also the general alignment of the toe in question which would also include the phalange bones.

Once the first piece and the second piece of the first metatarsal bone are aligned and the wire is inserted into the first piece with the desired alignment, an embodiment of an implant device may be provided.

An implant device is provided which may include an elongated framework which includes the intramedullary portion and the extramedullary portion, the extramedullary portion including at least one fastener aperture disposed to receive one or more bone fasteners to affix the extramedullary portion of the implant device to the second piece of the first metatarsal bone. Embodiments of the implant device are cannulated in that those embodiments have a contiguous wire aperture through both the intramedullary portion and the extramedullary portion of its framework. This allows the implant device to receive the wire in the wire aperture and slide down the second end of the wire with the intramedullary portion first. However, in other embodiments the wire aperture may provide interaction with the wire through a non-contiguous and/or intermittent wire aperture that extends partially or wholly throughout the length of the intramedullary portion.

Once the intramedullary portion reaches the location on the first piece of the first metatarsal bone where the wire protrudes, it can be forced or implanted into the first metatarsal bone with the already implanted portion of the wire serving as its directional guide and thereby aligning the implant device.

Once the intramedullary portion of the implant device is inserted or implanted into the first piece of the first metatarsal bone to the desired depth, the extramedullary portion of the implant device should be positioned alongside and/or abutting the desired surface of the second piece of the first metatarsal bone (with the second end of the wire protruding through the top of the wire aperture in the extramedullary portion of the implant device).

Fasteners may be placed through the fastener apertures in the extramedullary portion transversely to fasten the extramedullary portion to the second piece of the first metatarsal bone. It will be appreciated by those of ordinary skill in the art that any one of a number of different types of fasteners may be utilized to attach, fasten or secure the extramedullary portion of the implant device to the second piece of the first metatarsal bone, with no one particular being required to practice this invention. A preferred fastening mechanism is the use of bone screws or bone nails.

Once the proper alignment of the implant device has been achieved, the wire may be removed, although it does not have to be removed to practice this invention.

Figure 8:
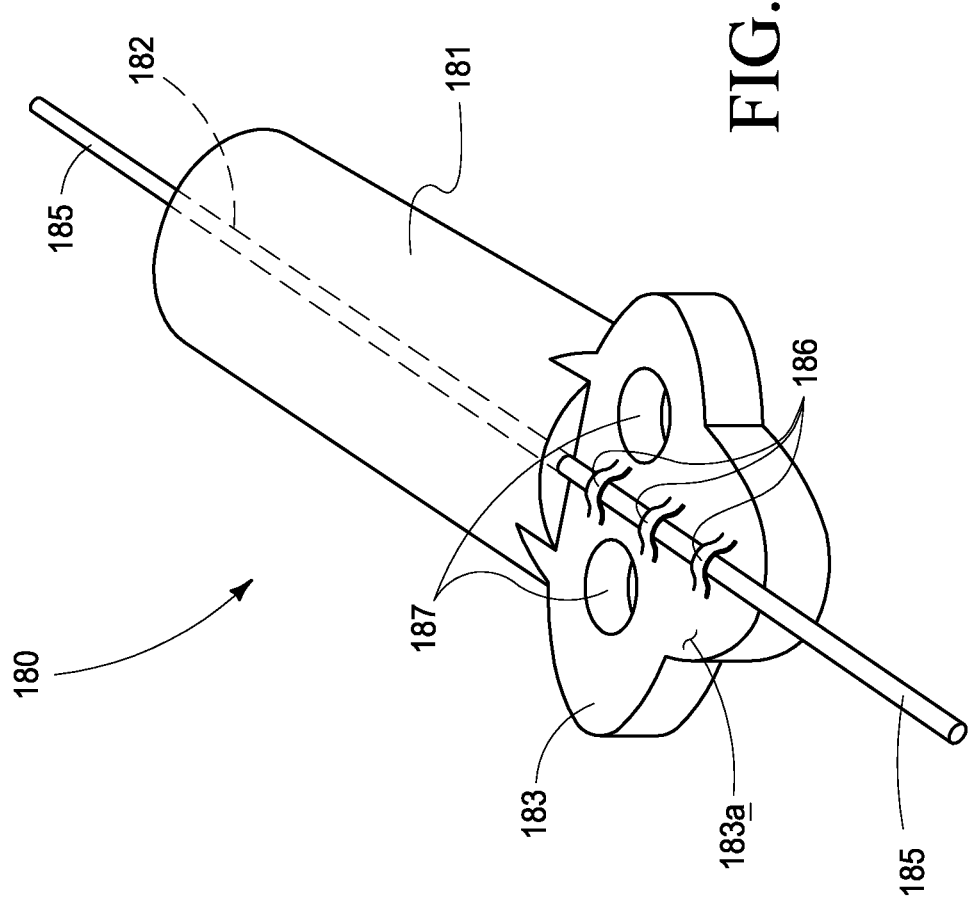
FIG. 8 is a perspective view of another example of another embodiment of an implant device contemplated by this invention.

FIG. 8 is a perspective view of another example of another embodiment of an implant device 180 contemplated by this invention. FIG. 8 illustrates implant device 180, intramedullary portion 181 of the implant device framework, as well as the extramedullary portion 183 of the implant device framework or body. The intramedullary portion 181 includes a wire or wire aperture 182 therethrough configured to receive and combine with wire 185 to provide alignment for the implant device via the wire 185.

Bone fastener apertures 187 through extramedullary portion 183 provide the aperture through which fasteners may be inserted transversely to then fasten the extramedullary portion 183 to a bone or piece of bone. FIG. 8 also illustrates that the wire aperture need not be fully closed, but must provide an appropriate aperture clearance or tolerance so that the wire 185 can combine with the wire aperture in the implant device to precisely align the implant device and assist in the alignment of the bones or pieces of bones that are being aligned or realigned as they are being fixed or stabilized by the implant device. FIG. 8 shows three guides 186 or bridges on the surface 183a of the extramedullary portion 183 and through which the wire 185 (which may also be referred to as a pin or K-wire) is inserted.

While FIG. 8 shows the intramedullary portion 181 without any transverse screw apertures, it should be noted that this embodiment may also be provided with transverse screw or other fastening apertures as shown in other figures, with this invention not being limited to any one such configuration.

Figure 9:
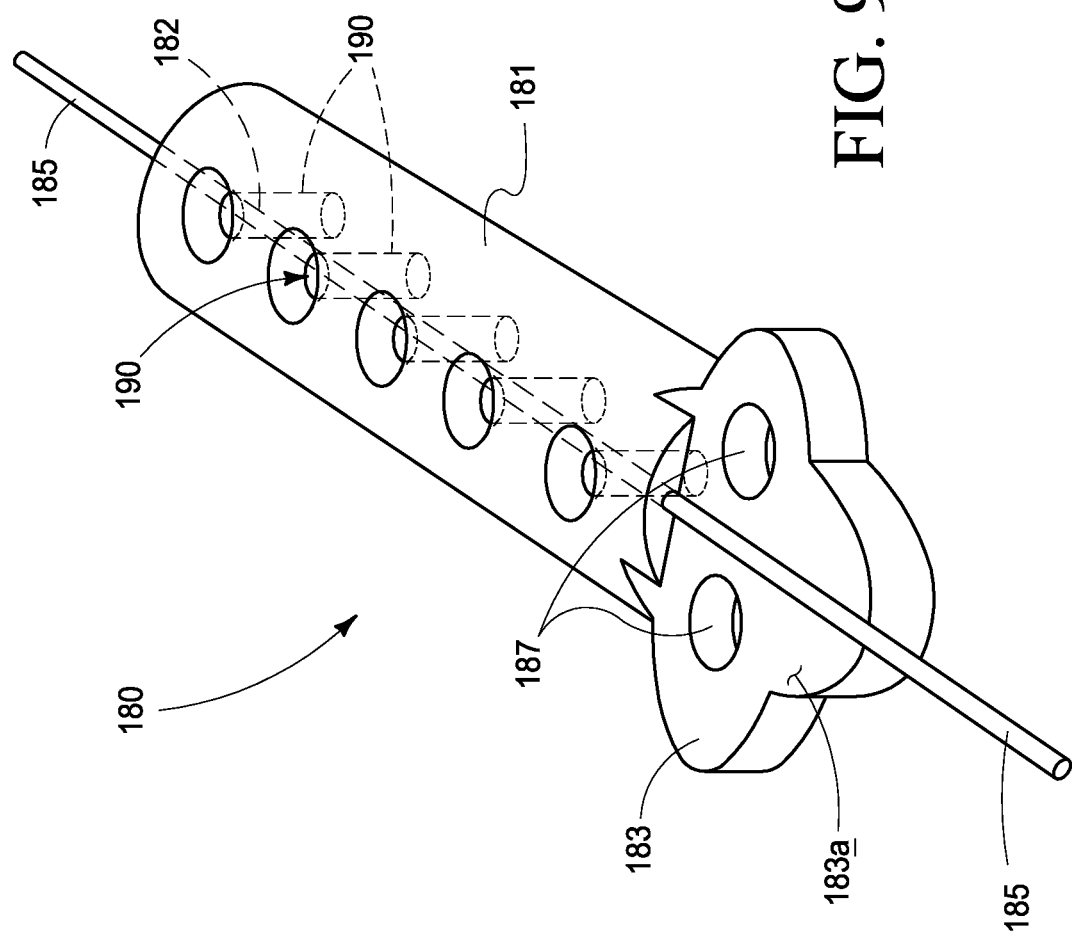
FIG. 9 is a perspective view of another example of an embodiment of an implant device contemplated by this invention wherein the k-wire aperture is only through the intramedullary portion of the implant device.

FIG. 9 is a perspective view of another example of an embodiment of an implant device 180 contemplated by this invention wherein the k-wire aperture 182 only extends through the intramedullary portion 181 of the implant device 180 and does not also extend through the extramedullary portion 183 as shown in other figures herein. The k-wire 185 in this example of an embodiment instead abuts or is adjacent to the surface 183a of the extramedullary portion 183.

FIG. 9 illustrates transverse apertures 190 (for fasteners or screws) through the intramedullary portion 181. The transverse apertures 190 may be normal or perpendicular to the axis of the intramedullary portion (or to the k-wire), or one or more of the transverse apertures may also be at an angle to facilitate for example the angles between the extramedullary portion and intramedullary portion illustrated in FIG. 11, FIG. 12 or FIG. 13, as examples. FIG. 9 also shows fastener apertures 187 in the extramedullary portion 183.

It should also be noted that there may be multiple transverse apertures in the intramedullary portion 181 of the implant device 180, with a first transverse aperture being at a dissimilar angle to a second transverse aperture, to achieve desired results according to the particular application of the invention.

FIG. 10 constitutes FIGS. 10A and 10B, which are different views of another embodiment of an implant device 200 contemplated by embodiments of this invention as described below relative to the description of FIGS. 10A and 10B.

Figure 13:
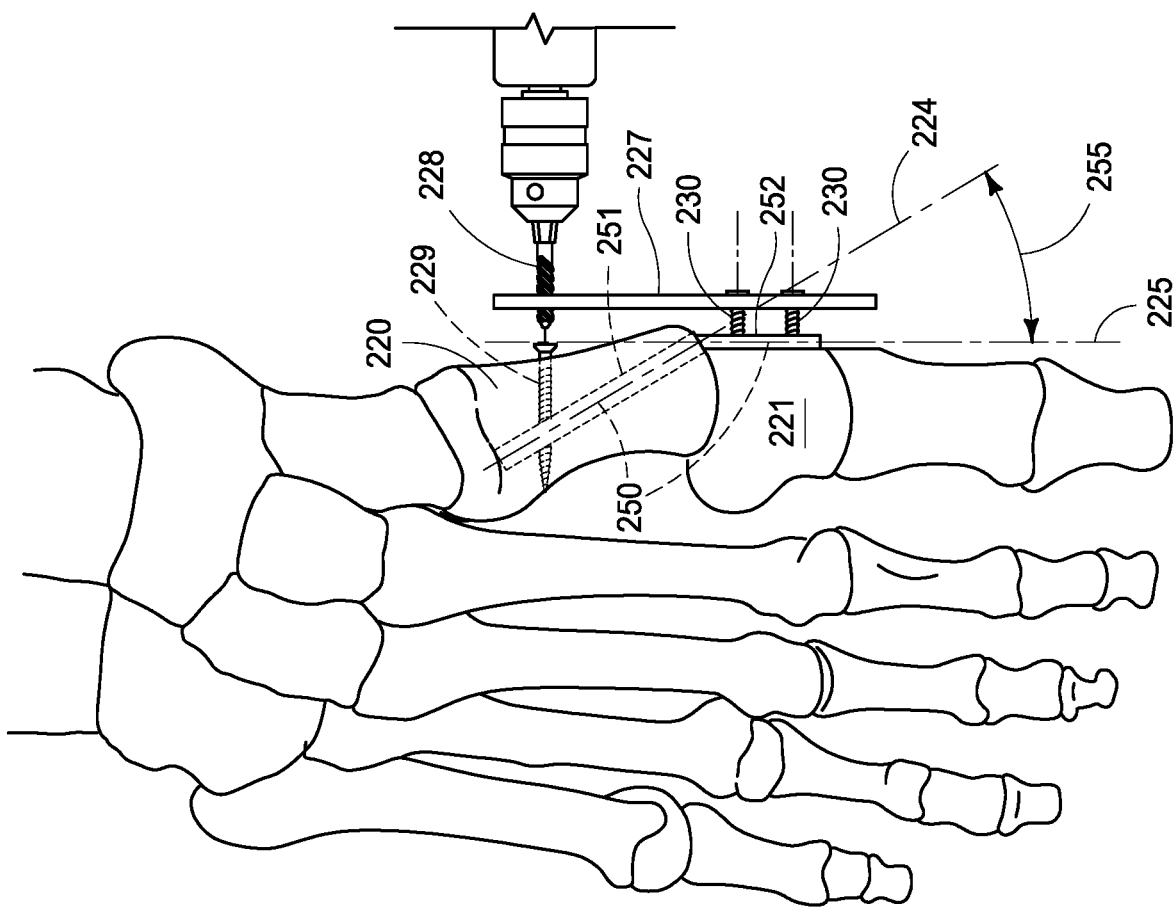

FIG. 10A is a top view and FIG. 10B is an elevation view of an example of another embodiment of an implant device 200 contemplated by this invention, illustrating extramedullary portion 202 with transverse apertures 203 (which may be used as fastener apertures as shown in FIG. 6, and/or as a means to attach a drill guide or template as shown in FIGS. 5 & 13, all within the contemplation of this invention), intramedullary portion 201 with a plurality of transverse fastener apertures 204.

FIG. 11 is a top view of an example of an embodiment of an implant device 210 contemplated by this invention, wherein the intramedullary portion 211 of the implant device 210 is at an angle 219 relative to the extramedullary portion 212. FIG. 11 shows extramedullary portion 212 with transverse apertures 213 (which may be used as fastener apertures as shown in FIG. 6, and/or as a means to attach a drill guide or template as shown in FIGS. 5 & 13, all within the contemplation of this invention), intramedullary portion 211 with a plurality of transverse fastener apertures 214. The angle 219 in this embodiment is the angle between the centerline or axis 218 of the intramedullary portion 211 and the angle of the centerline of the fastener apertures 213 and/or of the extramedullary portion 212. It may be desirable for some patient conditions to impart an angle such as angle 219 between the different parts of the metatarsal bone.

Figure 12:
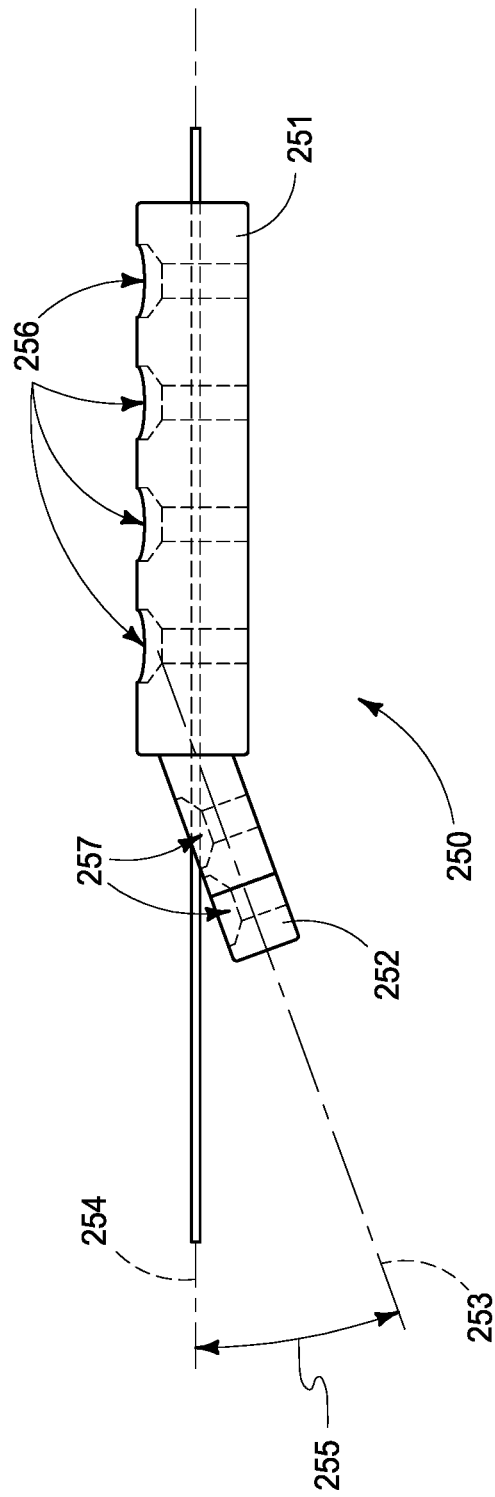
FIG. 12 is an elevation view of an example of another embodiment of an implant device contemplated by this invention, wherein the intramedullary portion of the implant device is at an angle relative to the extramedullary portion of the implant, only in a different plane than that illustrated in FIG. 11.

FIG. 12 is an elevation view of an example of another embodiment of an implant device 250 contemplated by this invention, wherein the intramedullary portion 251 of the implant device 250 is at an angle 255 relative to the extramedullary portion 252 of the implant 250, but the angle is in a different plane than the angle in FIG. 11. FIG. 12 illustrates extramedullary portion 252 with transverse apertures 257 (which may be used as fastener apertures as shown in FIG. 6, and/or as a means to attach a drill guide or template as shown in FIGS. 5 & 13, all within the contemplation of this invention), intramedullary portion 251 with a plurality of transverse fastener apertures 256. The angle 255 in this embodiment is the angle between the centerline or axis 254 of the intramedullary portion 251 and the downward angle of the centerline of the extramedullary portion 252. It may be desirable for some patient conditions to impart an angle, such as angle 255, between the different parts of the metatarsal bone (as shown in FIG. 13).

It should be noted that the particular angle desired may vary from patient to patient, and may be determined in advance of surgery, or altered during the course of the surgery to adapt to the angle of the bones and cuts made in or on the bones, all within the contemplation of embodiments of this invention. Known bending methods and devices may be utilized to bend or alter the angle such as shown as angle 255 in FIGS. 12 & 13.

FIG. 13 is top skeletal schematic representation of bones in a typical human foot, illustrating an example of an embodiment of an implant device 250 (one example of which is shown in FIG. 12) contemplated by embodiments of this invention, wherein a drill guide 227 or template is used to align the drilling of a hole to facilitate the insertion of a fastener 229 (a screw in this example) through the bone 220 and through the transverse fastener aperture in the intramedullary portion 251 of the implant device 250. This process may be practiced in a similar manner to that process described above regarding FIG. 5.

The drill guide 227 is a template to provide sufficient guidance and alignment of the drill 228 through the bone and through a fastener aperture in the screw (examples of which are shown in FIG. 12) such that the hole drilled through the bone aligns with the screw aperture in the intramedullary portion of the implant device. FIG. 13 shows the angle 255 between a centerline 224 of the intramedullary portion 251 and a centerline 225 of the extramedullary portion 252. Drill alignment guide 227 is shown fixed to the extramedullary portion 252 via screws 230, to secure the drill guide 227 in place to facilitate the drilling of a hole through the bone that aligns with the transverse fastener aperture (shown in other figures) in the intramedullary portion 251 of the implant 250. In this case the screws will be inserted at an angle to the intramedullary portion. The drill configuration is shown for illustration purposes only as there would not be drilling after the screw 229 is inserted, and is further not to scale—but instead the pilot hole for the screw would be drilled to the sizing, depth and configuration desired.

It will be noted and appreciated by those of ordinary skill in the art that the K-wire aperture or wire aperture may, but need not, be a fully enclosed uninterrupted aperture through both the intramedullary portion and the extramedullary portion of the implant device framework. The wire aperture or cannulated feature may also be dis-continuous in that there may be interruptions or breaks in the aperture so along as the wire is consistently located and surrounded to allow the wire to be used as an alignment device or mechanism for the implant device. The wire aperture therefore may be a less than complete slit through which the wire may be inserted and retained for the alignment purposes stated herein.

It should be noted that while the drawings and general description are directed toward the metatarsal bone in a foot, the implant device and method described herein may equally be used in other applications, with no one particular application being required to practice this invention.

Figure 14:
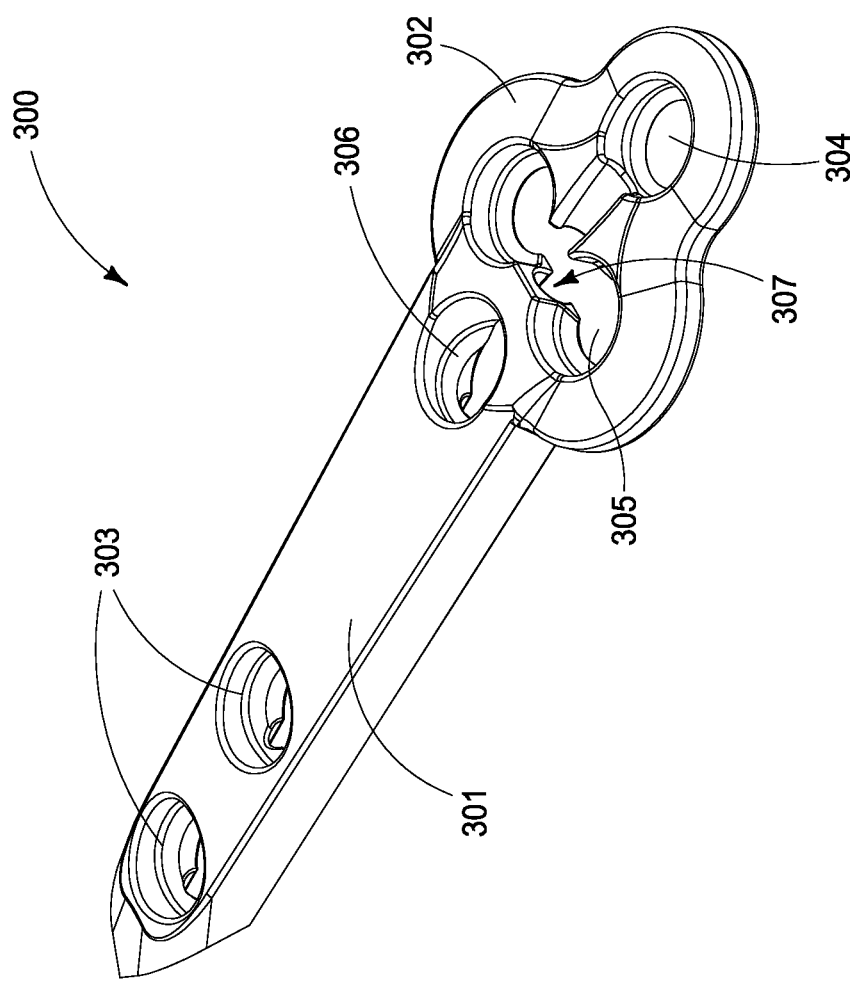
FIG. 14 is a perspective view of another example of an implant device contemplated by some embodiments of this invention.

FIG. 14 is a perspective view of another example of an implant device 300 contemplated by some embodiments of this invention, transverse fastener apertures 303 & 306, intramedullary portion 301, extramedullary portion 302, wire apertures 307, extramedullary fastener apertures 304 & 305.

FIG. 15 is a top view of the example of the implant device 300 illustrated in FIG. 14, illustrating intramedullary portion 301 and extramedullary portion 302. Like numbered items referenced in prior figures may not be repeated herein.

FIG. 16 is a front view of the example of the implant device 300 illustrated in FIG. 14, showing transverse fastener apertures 303 in the intramedullary portion 301 and transverse fastener aperture 304 in the extramedullary portion, the extramedullary portion 302 being at angle 310 relative to the axis of intramedullary portion 301. Like numbered items referenced in prior figures may not be repeated herein.

Figure 17:
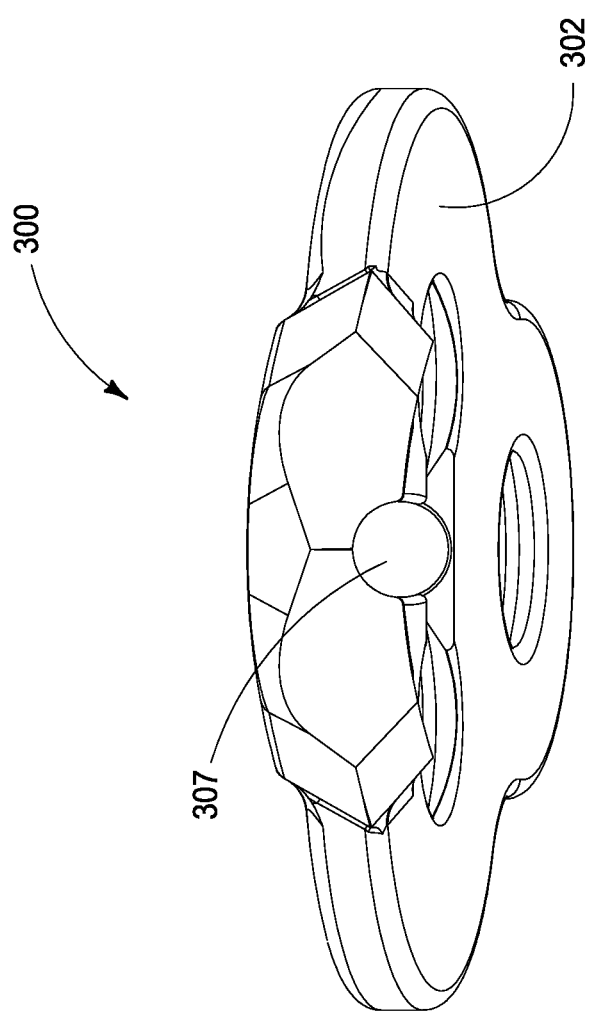
FIG. 17 is an end view of the example of the implant device illustrated in FIG. 14.

FIG. 17 is an end view of the example of the implant device 300 illustrated in FIG. 14, showing wire aperture 307 and extramedullary portion 302. A guide wire or K-wire may be utilized to position and or angle where the extramedullary portion is inserted into the metatarsal bone, and then the intramedullary portion may be inserted into the bone over the guide wire, and thereby positioned as guided by wire aperture 307. Like numbered items referenced in prior figures may not be repeated herein.

FIG. 18 is a bottom view of the example of the implant device 300 shown in FIG. 14, illustrating intramedullary portion 301, wire guide 307, extramedullary portion 302 and transverse fastener aperture 304 in the extramedullary portion 302. Like numbered items referenced in prior figures may not be repeated herein.

FIG. 19 is section view 19-19 from FIG. 18, illustrating the implant device 300 with wire guide aperture 307 and intramedullary portion 301.

Figure 20:
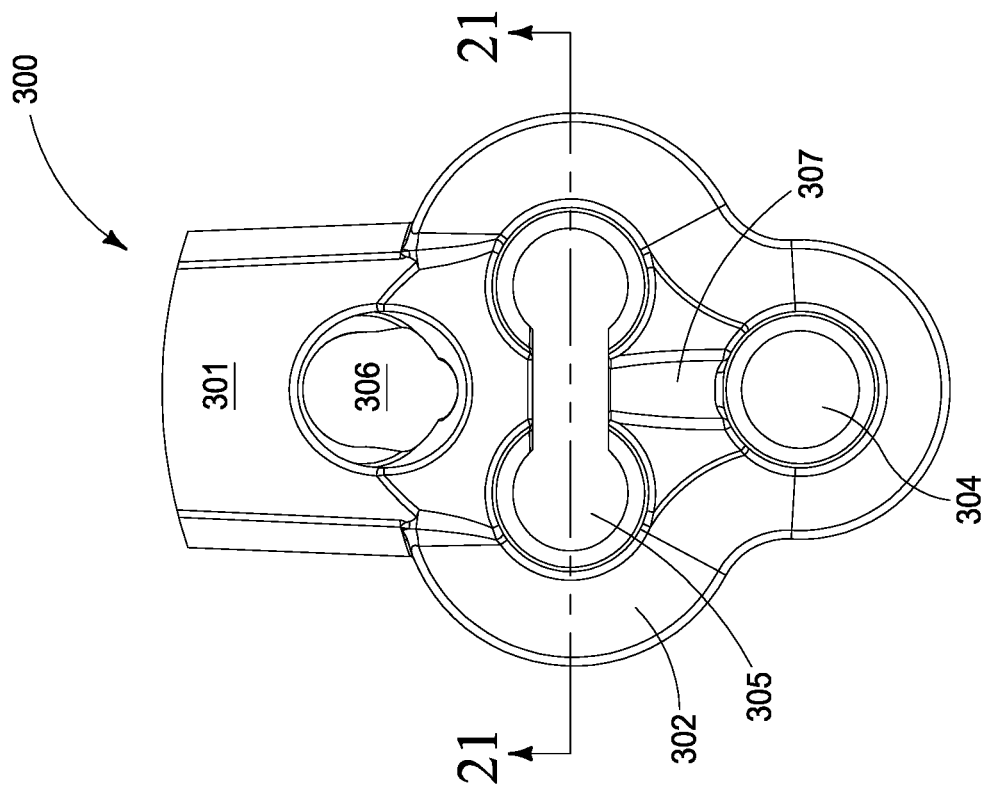
FIG. 20 is a top partial view of the implant device illustrated in FIG. 14.

FIG. 20 is a top partial view of the implant device 300 illustrated in FIG. 14, showing intramedullary portion 301, wire guide aperture 307, transverse fastener aperture 306, extramedullary portion 302, transverse fastener apertures 304 and 305 with extramedullary portion 302.

Figure 21:
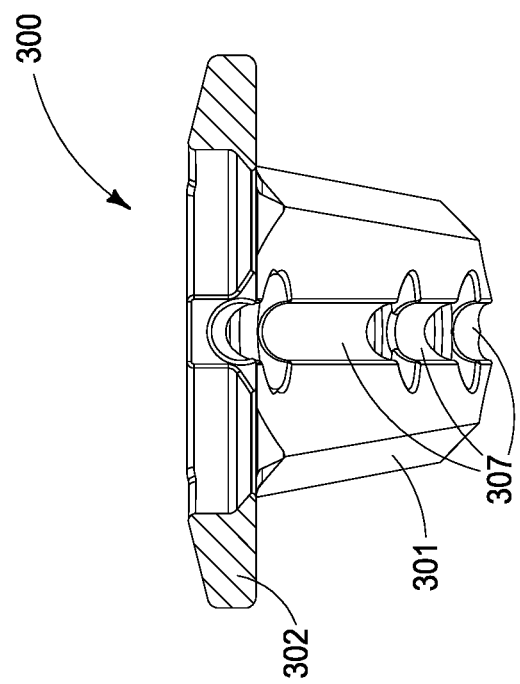
FIG. 21 is a section view 21-21 from FIG. 20.

FIG. 21 is a section view 21-21 from FIG. 20, illustrates implant device 300, extramedullary portion 302, intramedullary portion 301 and wire guide aperture 307.

Figure 22:
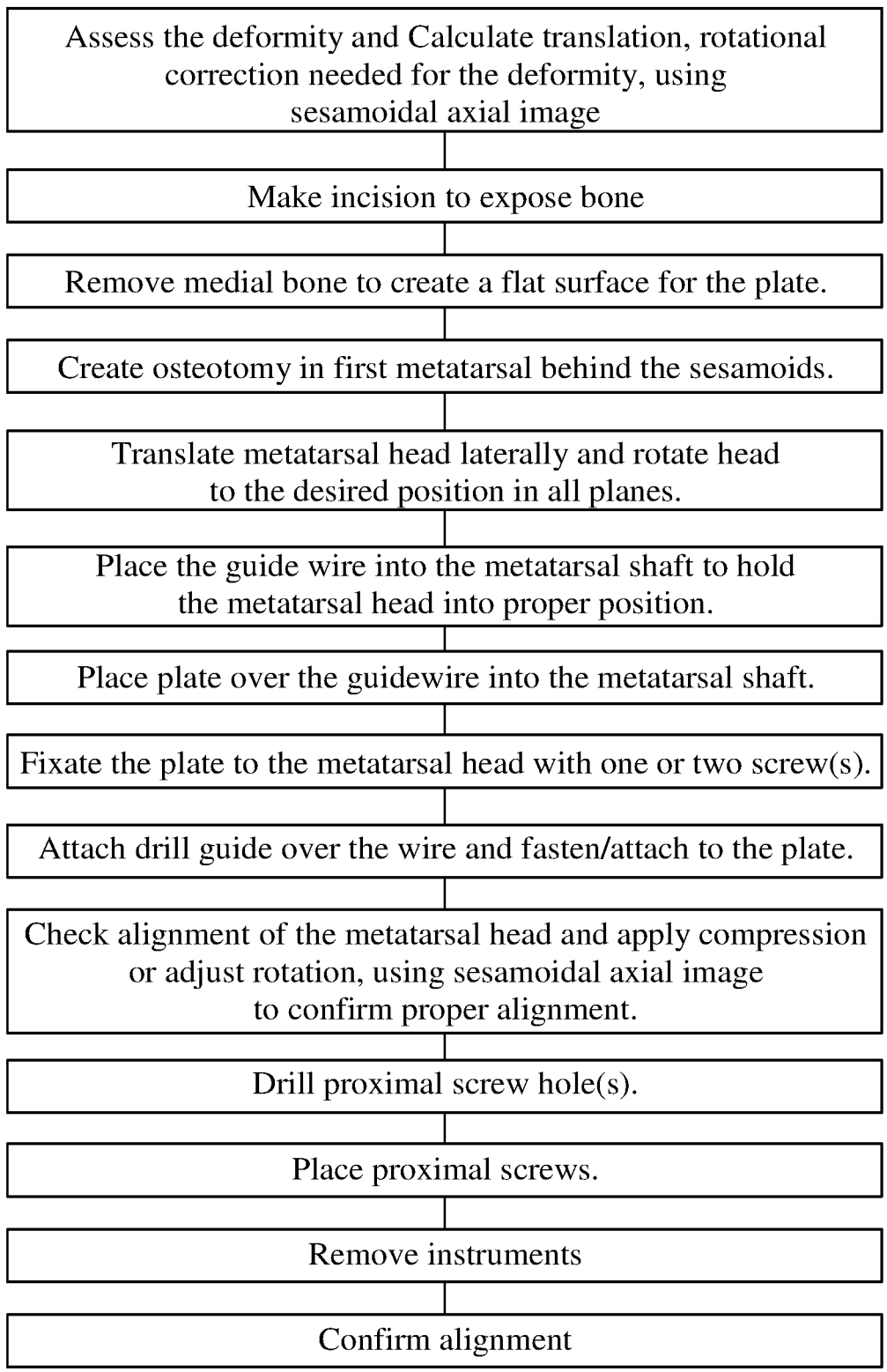
FIG. 22 is a box diagram flowchart of an example of a method contemplated by embodiments of this invention.

FIG. 22 is a box diagram flowchart of an example of an embodiment of a method contemplated by this invention. In the first step illustrated in FIG. 22, the deformity is assessed and the translation calculated, determining if and how much rotational correction may be needed for the deformity in question. Though this invention is not limited to it, a current tool in determining the translation and rotational correction is a sesamoidal axial image.

At that time an incision may be made to expose the bone which is to be operated on, and the medial bone is altered or a portion removed to create a surface (which may but need not be a flat surface) to prepare it for the fixation or attachment of the implant device. In embodiments of this invention, this would involve making a flat surface for the attachment of the plate portion of the implant device (the extramedullary portion).

A further step would be to then create an osteotomy in the first metatarsal behind the sesamoids, followed by the translation of the metatarsal head laterally and the rotation of the metatarsal head to the desired position in all planes.

Once the metatarsal head is in the desired position, the guide wire may be placed into the metatarsal shaft to hold the metatarsal head into proper position. Once the guide wire is placed and located as desired, the plate portion (extramedullary portion) may be placed over the guidewire into the metatarsal shaft.

At that stage the plate portion may be fixated to the metatarsal head with any one of a number of different fasteners, such as one or two screw(s).

The drill guide is preferably then attached over the guide wire and fastened/attached to the plate portion of the implant device.

Once the drill guide and other components are in place, an alignment check of the metatarsal head can be made and adjustments may be made for example by applying compression to move it to a more desired position, and/or a rotational force may be applied to rotationally adjust the position of the metatarsal head. During this process, known imaging equipment may be utilized to provide and use a sesamoidal axial image to confirm proper alignment.

An alignment tool may be utilized in embodiments of this invention to facilitate the compression and rotational adjustments. As described more fully below, the tool may be unitary or separate from the drill guide (preferably integral therewith), and would be attachable and detachable to the implant device already inserted in the metatarsal shaft to act as a targeting adjusting tool.

Once the final micro-adjustments have been made, the proximal screw holes may be drilled as desired and the proximal screws may be placed or inserted.

The instruments may then be removed, final alignment positioning confirmed and the incisions may then be closed.

Figure 23:
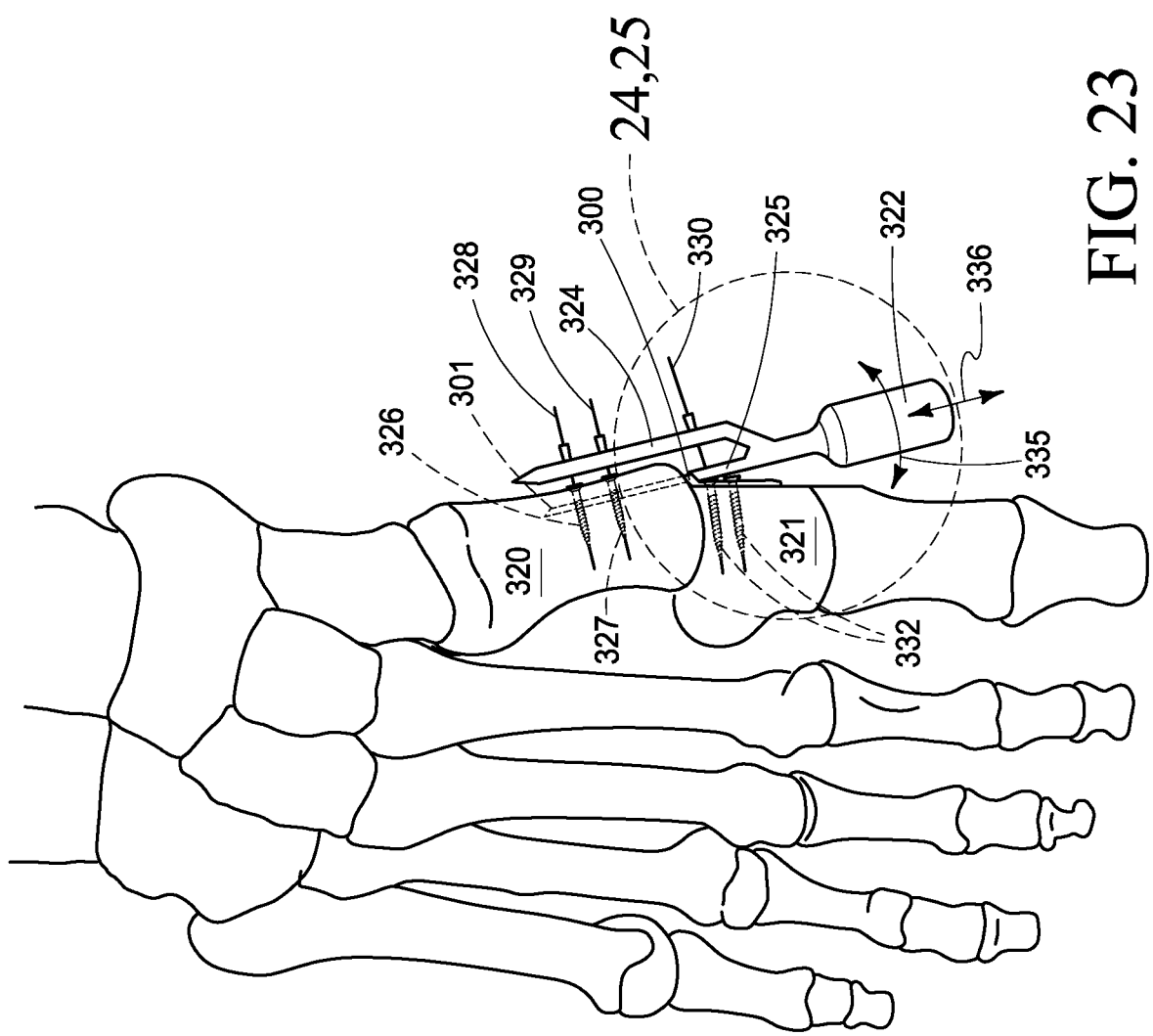
FIG. 23 is a top view of an example of the implanting of the implant device illustrated in FIG. 14, showing among other things, an alignment tool.

FIG. 23 is a top view of an example of the implanting of the implant device 300 illustrated in FIG. 14, showing among other things, an alignment tool comprised of handle 322, transverse or proximal screw guide portion 324 and implant device attachment portion 325. FIG. 23 shows the extramedullary portion of the implant device 300 fastened metatarsal head 321 via cannulated screws 332 with an exemplary guide wires 330 (for the extramedullary portion) and exemplary guide wires 328 & 329 for the intramedullary portion. FIG. 23 further shows how the proximal screw guide portion 324 is utilized with alignment guide wires 328 and 329, with cannulated screws 326 and 327 being placed or fastened into bone 320 once the proper positioning alignment has been achieved, as set forth and described elsewhere herein. Arrow 335 illustrates how the alignment tool may be rotated to place the implant device in the desired rotationally aligned position and arrow 336 illustrates how the alignment tool may be moved laterally or on a plane to place the implant device in the desired position.

Figure 24:
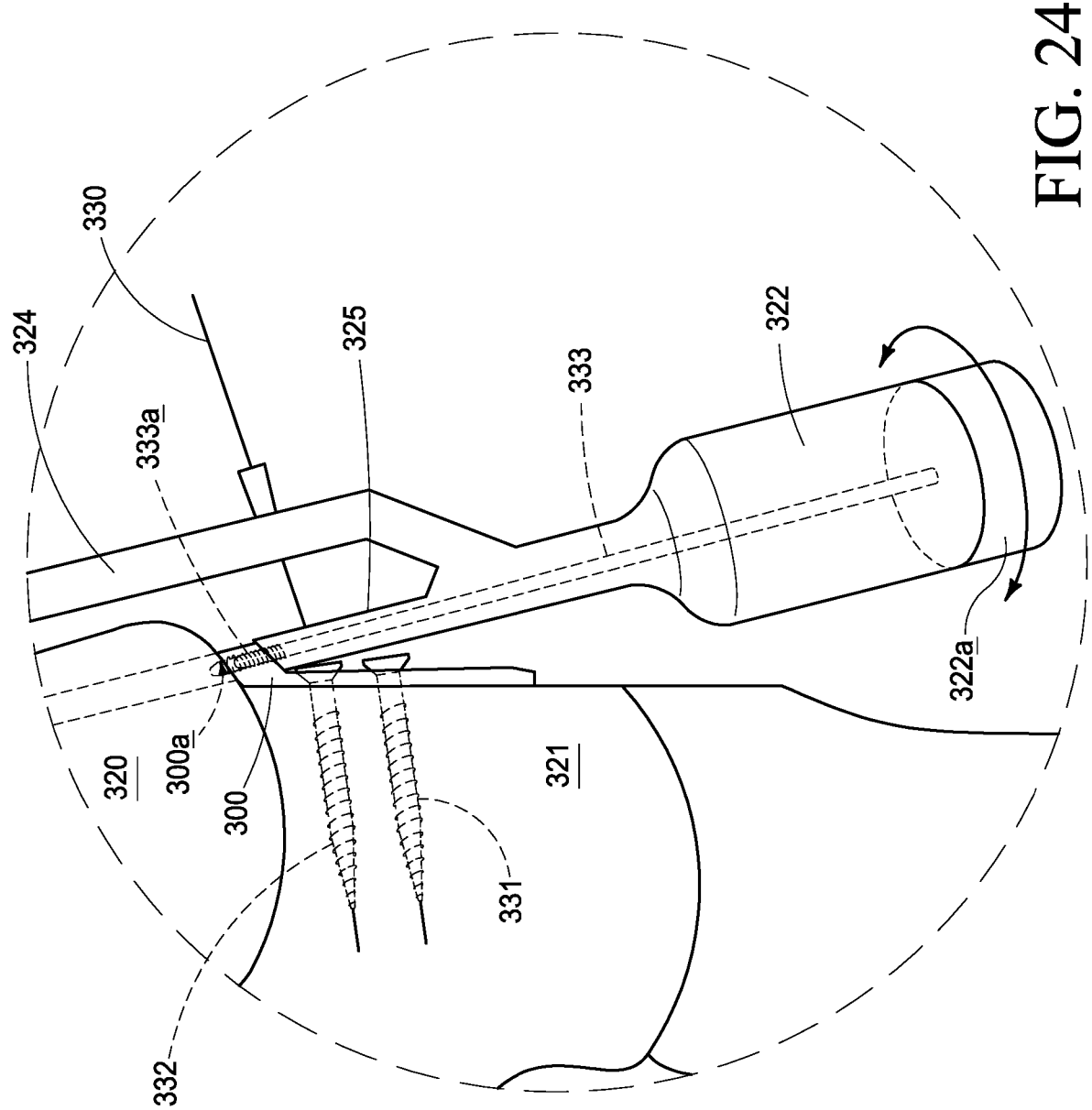
FIG. 24 is the referenced detail view from FIG. 23.

FIG. 24 is detail view from FIG. 23, and illustrates an example of one embodiment that may be utilized to practice this invention. FIG. 24 shows handle 322 with a shaft 333 extending there through, the shaft 333 being externally threaded at 333a and operably attached to a rotatable end 322a of handle 322. The surgeon can then rotate the rotatable end 322a to thereby cause the external threads 333a to engage in internally threaded aperture 300a in the implant device.

The configuration illustrated in FIG. 24 allows the surgeon to fix the handle to the implant device before the proximal screws are fixed and thereby manipulate the location and rotational angle of the implant device to the most desired location, as described more fully above. Although a threaded attachment and detachment mechanism or means is illustrated, it will be appreciated by those of ordinary skill in the art that any one of a number of attachable and detachable fastening mechanisms and means may be utilized, all within the contemplation of this invention, with no one being required to practice this invention. Aspects or embodiments of an implant alignment tool as shown in FIG. 24 may include an externally threaded shaft 333 configured to fasten to and unfasten from to an internally threaded aperture 300a in the implant device. One way to practice this embodiment of the invention is to further rotatably mount the shaft 333 relative to the handle 322 of the implant alignment tool such that it can be rotated (as shown by the arrow) to fasten it to the implant device and rotated an opposite direction to unfasten it from the implant device.

Figure 25:
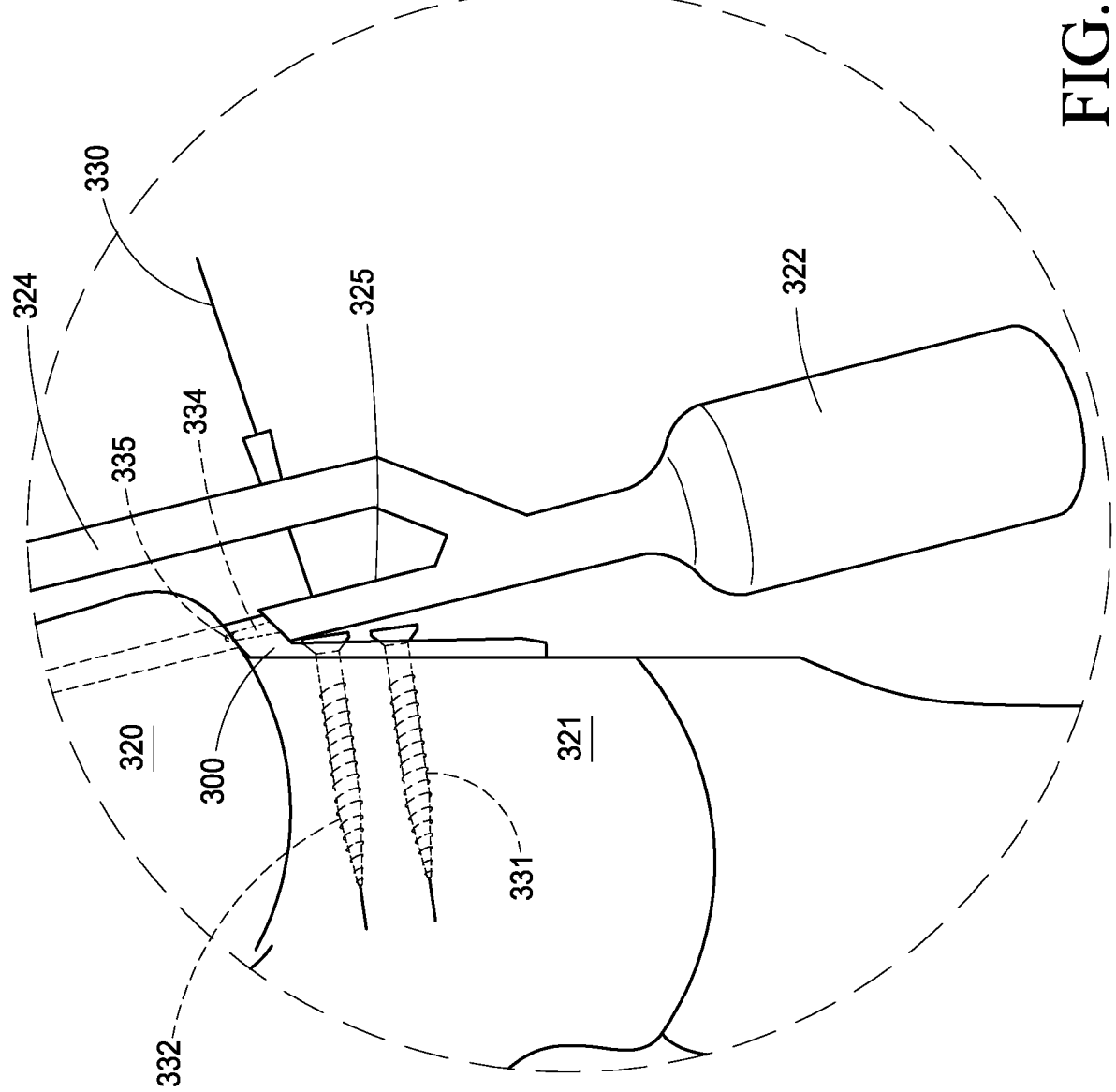
FIG. 25 is an alternative detail view from FIG. 23, which is another aspect or embodiment of that shown.

FIG. 25 is an alternative detail view from FIG. 23, which is an example of another way to practice an embodiment of this invention wherein the alignment tool is attachable and detachable to the implant device 300. In FIG. 25, the alignment tool aperture 335 in the implant device 300 receives attachment protrusion 334 which is part of the alignment tool, and the aperture 335 in the implant device is sized and/or shaped (such as by a truncated configuration—but not limited thereto) so that a solid fixed connection may occur to manipulate the implant device 300, before detaching it. In one aspect or example of this embodiment, a shaft 334 is sized relative to a shaft aperture 335 in the implant device such that the implant alignment tool may be fastened to and unfastened from the implant device via a friction fit.

As will be appreciated by those of reasonable skill in the art, there are numerous embodiments to this invention, and variations of elements and components which may be used, all within the scope of this invention. In one embodiment for example, an implant device configured for implanting in a patient to align or stabilize a first bone section relative to a second bone section of a patient, the implant comprising: an elongated framework including an intramedullary portion integral with an extramedullary portion, configured to attach a first bone section to a second bone section; the intramedullary portion configured for insertion into the first bone section and including at least one fastener aperture configured to transversely receive a bone fastener there-through; the extramedullary portion configured to abut a surface of the second bone section and including at least one fastener aperture disposed to transversely receive a bone fastener inserted in the second bone section; a wire aperture through the intramedullary portion of the framework, disposed to receive and be guided by a wire inserted in the first bone section as the intramedullary portion is inserted into the first bone.

In addition to the embodiment disclosed in the preceding paragraph, further embodiments may be: further wherein the contiguous wire aperture is a slit in the framework; further wherein the contiguous wire aperture is a fully enclosed guide or cannula in the framework; further wherein the contiguous wire aperture is a continuous fully enclosed aperture in the framework; further wherein the intramedullary portion is generally circular or oval and the extramedullary portion is a plate; further wherein the at least one fastener aperture is comprised of a first fastener aperture and a second fastener aperture spaced apart on the extramedullary portion of the framework (further wherein the first and second fastener apertures are configured to combine with a first bone fastener inserted through the first fastener aperture and a second bone fastener inserted through the second fastener aperture, to secure the extramedullary portion of the framework to the first bone of the patient); further wherein the first bone of the patient is a first piece of the first metatarsal bone and the second bone of the patient is a second piece of the first metatarsal bone; further wherein the extramedullary portion includes a wire aperture also disposed to receive and be guided by the wire inserted in the first bone section as the intramedullary portion is inserted into the first bone section, the wire aperture in the extramedullary portion being contiguous with the wire aperture in the intramedullary portion; further wherein the extramedullary portion is bent at an angle relative to the intramedullary portion such that it is disposed to affix to a surface of the second bone section; further wherein the extramedullary portion is bent at a transverse angle relative to the intramedullary portion such that it is disposed to affix to a surface of the second bone section; and/or further wherein the wire is a k-wire.

In another embodiment, a method embodiment, a method to re-align and stabilize a patient's metatarsal bone may be provided which comprises: transversely severing the first metatarsal bone at a desired location, resulting in a first piece and a second piece of the first metatarsal bone; placing the second piece of the first metatarsal bone in the desired alignment with the first piece; inserting a first end of a wire into the first piece of the first metatarsal bone at a desired angle and such that a second end of the wire is substantially aligned alongside the second piece; providing an implant device comprised of: an elongated framework including an intramedullary portion and an extramedullary portion, the extramedullary portion including at least one fastener aperture disposed to transversely receive a bone fastener to affix the extramedullary portion to the second piece of the first metatarsal bone; and a contiguous wire aperture axially through the intramedullary portion; sliding the wire aperture of the intramedullary portion over the second end of the wire and sliding the implant device over the wire until the intramedullary portion of the implant device is implanted into the first piece of the metatarsal bone; and fastening the extramedullary portion of the implant device to the second piece of the first metatarsal bone by inserting a fastener through the at least one fastener aperture and into the second piece of the first metatarsal bone; and fastening the intramedullary portion of the implant device to the first piece of the first metatarsal bone by inserting a fastener through the at least one fastener aperture and into the first piece of the first metatarsal bone.

In addition to the embodiment disclosed in the preceding paragraph, further embodiments may be: further comprising the step of reforming the first piece of the metatarsal bone to provide a surface which disposes it to better attach to the extramedullary portion of the implant device; further wherein the reforming of the first piece of the metatarsal bone includes cutting a substantially planar surface disposed for abutment to the extramedullary portion of the implant device; further comprising bending the extramedullary portion relative to the intramedullary portion such that the extramedullary portion more desirably abuts substantially planar surface on the second piece of the patient's metatarsal bone; further comprising the step of using the wire alignment angle to align the insertion of the intramedullary portion into the first piece of the metatarsal bone; further comprising the step of using the wire alignment angle to align the position of the extramedullary portion of the implant device relative to the mounting location on the second piece of the metatarsal bone; further wherein the bone fastener is a bone screw; further wherein the step of fastening the intramedullary portion of the implant device to the first piece of the first metatarsal bone by inserting a fastener through the at least one fastener aperture and into the first piece of the first metatarsal bone, is performed before the step of fastening the extramedullary portion of the implant device to the second piece of the first metatarsal bone by inserting a fastener through the at least one fastener aperture and into the second piece of the first metatarsal bone; and/or further wherein the step of fastening the intramedullary portion of the implant device to the first piece of the first metatarsal bone by inserting a fastener through the at least one fastener aperture and into the first piece of the first metatarsal bone, further comprises: fixing a drill guide to the extramedullary portion, the drill guide including a drill aperture which is thereby fixed and aligned relative to the transverse fastener aperture in the intramedullary portion such that a pilot hole may be drilled through a portion of the first bone piece and through the transverse fastener aperture in the intramedullary portion, thereby furthering the securement of the intramedullary portion to the first bone piece.

In yet a more general method embodiment, a method to re-align and stabilize a patient's bone may be provided which comprises: transversely severing the patient's bone at a desired location, resulting in a first piece and a second piece of the patient's bone; placing the second piece of the patient's bone in the desired alignment with the first piece; inserting a first end of a wire into the first piece of the patient's bone at a desired angle and such that a second end of the wire is substantially aligned alongside the second piece; providing an implant device comprised of: an elongated framework including an intramedullary portion and an extramedullary portion, the extramedullary portion including at least one fastener aperture disposed to transversely receive a bone fastener to affix the extramedullary portion to the second piece of the patient's bone; and a contiguous wire aperture axially through the intramedullary portion; sliding the wire aperture of the intramedullary portion over the second end of the wire and sliding the implant device over the wire until the intramedullary portion of the implant device is implanted into the first piece of the patient's bone; and fastening the extramedullary portion of the implant device to the second piece of the patient's bone by inserting a fastener through the at least one fastener aperture and into the second piece of the patient's bone; and fastening the intramedullary portion of the implant device to the first piece of the patient's bone by inserting a fastener through the at least one fastener aperture and into the first piece of the patient's bone.

In another embodiment, an implant alignment tool may be provided for use in combination with an implant device, configured for aligning an implant device in a patient being implanted to stabilize a first bone section relative to a second bone section of a patient, the implant alignment tool comprising: a handle; a proximal screw guide portion extending from said handle; and an implant device attachment portion.

Additional embodiments from those in the preceding paragraph may include such an implant alignment tool: wherein the implant device attachment portion is further comprised of an externally threaded shaft configured to fasten to and unfasten from to an internally threaded aperture in the implant device, and optionally further wherein the shaft is rotatably mounted relative to the handle of the implant alignment tool such that it can be rotated to fasten it to the implant device and rotated an opposite direction to unfasten it from the implant device.

An additional embodiment from that described in the second preceding paragraph may be further wherein the shaft is sized relative to a shaft aperture in the implant device such that the implant alignment tool may be fastened to and unfastened from the implant device via a friction fit.

Another method embodiment may include a method to re-align and stabilize a patient's metatarsal bone comprising: assessment of a deformity to be remedied, including the desired translational and rotational correction; make incision to expose the metatarsal bone; remove a medial bone to create an appropriate surface for receiving a portion of an implant device; create an osteotomy in a first metatarsal bone behind the sesamoids; translate the metatarsal head laterally and rotate head to the desired position in all planes; place a guide wire into a shaft of the metatarsal bone to locate the metatarsal head into a desired position; providing an implant device comprised of: an elongated framework including an intramedullary portion and an extramedullary portion, the extramedullary portion including at least one fastener aperture disposed to transversely receive a bone fastener to affix the extramedullary portion to the second piece of the first metatarsal bone; and a contiguous wire aperture axially through the intramedullary portion; place the extramedullary portion over the guide wire and into the shaft of the metatarsal; fixate the extramedullary portion to the metatarsal head with one or more fasteners; attach a drill guide over the wire and fast the drill guide to the extramedullary portion; evaluate and adjust the alignment of the metatarsal head utilizing the implant adjustment tool; drill proximal fastener apertures in the metatarsal bone; and place proximal fasteners into the metatarsal bone.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method to re-align and stabilize a patient's metatarsal bone comprising:
   assessing of a deformity to be remedied, including an intermediate or final translational and rotational correction;
   making an incision to expose the metatarsal bone;
   creating an osteotomy in the metatarsal bone behind the sesamoids thereby separating a metatarsal head from a metatarsal shaft of the metatarsal bone;
   creating a surface on the metatarsal head for affixing an extramedullary portion of an implant device;
   translating the metatarsal head laterally and rotating the metatarsal head to the intermediate or final position in all planes;
   placing a guide wire into the shaft of the metatarsal bone for locating the metatarsal head into the intermediate or final position;
   wherein the implant device is comprised of:
      an elongated framework including an intramedullary portion and the extramedullary portion,
      the extramedullary portion including at least one transverse fastener aperture disposed to transversely receive at least one bone fastener to affix the extramedullary portion to the surface on the metatarsal head;
      the intramedullary portion including at least one transverse fastener aperture disposed to transversely receive at least one bone fastener to affix the intramedullary portion to the shaft of the metatarsal bone; and
      a contiguous wire aperture axially through the intramedullary portion;
   placing the intramedullary portion over the guide wire and into the shaft of the metatarsal bone;
   affixing the extramedullary portion to the metatarsal head with at least one bone fastener;
   attaching a drill guide over the guide wire and fastening the drill guide to the extramedullary portion;
   evaluating and adjusting the alignment of the metatarsal head relative to the shaft of the metatarsal bone to achieve a final angle there-between through the utilization of an implant adjustment tool;
   drilling at least one proximal fastener aperture in the shaft of the metatarsal bone; and
   placing at least one bone fasteners into the shaft of the metatarsal bone and through the at least one transverse fastener aperture in the intramedullary portion.

2. The method to re-align and stabilize a patient's metatarsal bone as recited in claim 1, and further wherein the assessment of the deformity to be remedied is made utilizing a sesamoidal axial image.

3. The method to re-align and stabilize a patient's metatarsal bone as recited in claim 2, and further wherein the metatarsal head is altered to provide a surface disposed to affix the extramedullary portion of the implant device thereto.

4. The method to re-align and stabilize a patient's metatarsal bone as recited in claim 1, and further comprising the steps of confirming the intermediate or final alignment of the shaft and the head of the metatarsal bone and then closing the incision.

5. The method to re-align and stabilize a patient's metatarsal bone as recited in claim 4, and further comprising bending the extramedullary portion relative to the intramedullary portion to re-position the extramedullary portion relative to the surface on the metatarsal head of the patient's metatarsal bone.

6. The method to re-align and stabilize a patient's metatarsal bone as recited in claim 1, and further comprising the step of using a final determined angle between the guide wire and the surface on the metatarsal head to align the placement of the intramedullary portion over the guide wire and into the shaft of the metatarsal bone.

7. The method to re-align and stabilize a patient's metatarsal bone as recited in claim 1, and further comprising the step of using a final determined angle between the guide wire and the surface on the metatarsal head to align the position of the extramedullary portion of the implant device relative to the mounting location on the metatarsal head.

8. The method to re-align and stabilize a patient's metatarsal bone as recited in claim 1, and further wherein the at least one bone fastener affixing the intramedullary portion, and the at least one bone fastener fastener affixing the extramedullary portion to the surface are bone screws.

9. The method to re-align and stabilize a patient's metatarsal bone as recited in claim 1, and further wherein the steps of drilling at least one proximal fastener aperture in the shaft of the metatarsal bone and placing at least one bone fasteners into the shaft of the metatarsal bone and through the at least one transverse fastener aperture in the intramedullary portion are performed before the step of fastening the extramedullary portion of the implant device to the of the metatarsal bone by inserting a fastener through the at least one fastener aperture in the extramedullary portion and into the head of the metatarsal bone.

10. The method to re-align and stabilize a patient's metatarsal bone as recited in claim 1, and further wherein the step of fastening the intramedullary portion of the implant device to the shaft of the metatarsal bone by inserting a bone fastener through the at least one fastener aperture and into the shaft of the metatarsal bone, further comprises:
   the drill guide including a drill aperture which is thereby fixed and aligned relative to the at least one transverse fastener aperture in the intramedullary portion such that a pilot hole may be drilled through a portion of the shaft of the metatarsal bone and through the at least one transverse fastener aperture in the intramedullary portion, thereby furthering the securement of the intramedullary portion to the shaft of the metatarsal bone.

11. The method to re-align and stabilize a patient's metatarsal bone as recited in claim 1, and further wherein the guide wire is removed before the evaluating and adjusting the alignment of the metatarsal head relative to the shaft of the metatarsal bone with the implant adjustment tool.

12. The method to re-align and stabilize a patient's metatarsal bone as recited in claim 1, and further wherein the guide wire is removed after the evaluating and adjusting the alignment of the metatarsal head relative to the shaft of the metatarsal bone with the implant adjustment tool.

* * * * *